(12) United States Patent
Yamamichi

(10) Patent No.: US 8,727,619 B2
(45) Date of Patent: May 20, 2014

(54) RADIOGRAPHIC IMAGE CAPTURING SYSTEM

(75) Inventor: Youji Yamamichi, Hachioji (JP)

(73) Assignee: Konica Minolta Medical & Graphic, Inc. (JP)

( * ) Notice: Subject to any disclaimer, the term of this patent is extended or adjusted under 35 U.S.C. 154(b) by 342 days.

(21) Appl. No.: 13/306,176

(22) Filed: Nov. 29, 2011

(65) Prior Publication Data

US 2012/0145914 A1 Jun. 14, 2012

(30) Foreign Application Priority Data

Dec. 9, 2010 (JP) ................................. 2010-274340

(51) Int. Cl.
*G01D 18/00* (2006.01)
(52) U.S. Cl.
USPC ........................................................ 378/207
(58) Field of Classification Search
CPC .......... A61B 6/58; A61B 6/582; A61B 6/585; H05G 1/26
USPC ..................................... 378/207; 250/252.1
See application file for complete search history.

(56) References Cited

U.S. PATENT DOCUMENTS 7,298,825 B2 * 11/2007 Omernick et al. ............ 378/116
8,021,047 B2 * 9/2011 Yoshida et al. ............... 378/207

FOREIGN PATENT DOCUMENTS

| JP | 6-342099 A | 12/1994 |
| JP | 2000-139889 A | 5/2000 |
| JP | 3639750 B2 | 1/2005 |
| JP | 2006-58124 A | 3/2006 |
| JP | 2010-112866 A | 5/2010 |

* cited by examiner

*Primary Examiner* — Jurie Yun
(74) *Attorney, Agent, or Firm* — Cantor Colburn LLP

(57) ABSTRACT

Disclosed is an radiographic image capturing system, which makes it possible to establish second β*-correction data for the replacement-use radiographic image capturing apparatus, even if a console is busy. The system includes: a radiographic image capturing apparatus provided with radiation detecting elements two dimensionally arranged, to output image data representing a radiographic image; a radiation source to emit radiation; a cradle provided in an image capturing room; and a console to create a radiographic image based on the image data. When the replacement-use radiographic image capturing apparatus is inserted into the cradle, the cradle reads out first β-correction data, therefrom, and then, based on the first β-correction data, the first α-correction data and second α*-correction data, the cradle calculates second β*-correction data corresponding to the radiation source currently residing in the image capturing room, so as to establish the second β*-correction data above-calculated for the replacement-use radiographic image capturing apparatus.

8 Claims, 15 Drawing Sheets

FIG. 11

| IMAGE CAPTURING ORDER ID | PATIENT ID | PATIENT NAME | PATIENT SEX | PATIENT AGE | DIAGNOSIS AND TREATMENT DEPARTMENT | IMAGE CAPTURING PORTION | IMAGE CAPTURING DIRECTION | BUCKY TABLE ID | CASSETTE ID |
|---|---|---|---|---|---|---|---|---|---|
| 001 | 100085 | A | MALE | 25 | ORTHOPEDIC SURGERY | ABDOMEN | FRONT SURFACE P→A | 002 | FPD-003 |
| 002 | 100085 | A | MALE | 25 | ORTHOPEDIC SURGERY | BREAST | FRONT SURFACE P→A | 001 | FPD-001 |
| 003 | 100085 | A | MALE | 25 | ORTHOPEDIC SURGERY | CERVICAL VERTEBRAE | FRONT SURFACE P→A | 001 | FPD-001 |
| 004 | 100085 | A | MALE | 25 | ORTHOPEDIC SURGERY | BRACHIAL REGION | L | 003 | FPD-002 |
| 005 | 100101 | B | MALE | 45 | SURGERY | BREAST | SIDE SURFACE R→L | 001 | CR-001 |
| 006 | 100063 | C | FEMALE | 32 | SURGERY | ABDOMEN | FRONT SURFACE P→A | 002 | FPD-004 |

PLEASE INPUT IMAGE CAPTURING ORDER INFORMATION OF SCHEDULED IMAGE CAPTURING OPERATION

| | IMAGE CAPTURING ORDER ID (P1) | PATIENT ID (P2) | PATIENT NAME (P3) | PATIENT SEX (P4) | PATIENT AGE (P5) | DIAGNOSIS AND TREATMENT DEPARTMENT (P6) | IMAGE CAPTURING PORTION (P7) | IMAGE CAPTURING DIRECTION (P8) | BUCKY TABLE ID (P9) | CASSETTE ID (P10) |
|---|---|---|---|---|---|---|---|---|---|---|
| ● | 001 | 100085 | A | MALE | 25 | ORTHOPEDIC SURGERY | ABDOMEN | FRONT SURFACE P→A | 002 | FPD-003 |
| ○ | 002 | 100085 | A | MALE | 25 | ORTHOPEDIC SURGERY | BREAST | FRONT SURFACE P→A | 001 | FPD-001 |
| ○ | 003 | 100085 | A | MALE | 25 | ORTHOPEDIC SURGERY | CERVICAL VERTEBRAE | FRONT SURFACE P→A | 001 | FPD-001 |
| ○ | 004 | 100085 | A | MALE | 25 | ORTHOPEDIC SURGERY | BRACHIAL REGION | L | 003 | FPD-002 |
| ○ | 005 | 100101 | B | MALE | 45 | SURGERY | BREAST | SIDE SURFACE R→L | 001 | CR-001 |
| ○ | 006 | 100063 | C | FEMALE | 32 | SURGERY | ABDOMEN | FRONT SURFACE P→A | 002 | FPD-004 |

DETERMINATION    RETURN

RADIOGRAPHIC IMAGE CAPTURING SYSTEM

This application is based on Japanese Patent Application NO. 2010-274340 filed on Dec. 9, 2010, with the Japan Patent Office, the entire content of which is hereby incorporated by reference.

BACKGROUND OF THE INVENTION

The present invention relates to a radiographic image capturing system.

Various kinds of radiographic images, which are represented by an X-ray image captured by using X-ray radiation, have been widely employed for the purpose of diagnosing a disease or the like. This kind of medical radiographic images as abovementioned have been captured by using a screen film. However, in order to promote the digitalization trend of the radiographic image, the CR (Computed Radiography) apparatus that employs a photostimulable phosphor sheet had been developed, and in recent years, there has been developed such the radiographic image capturing apparatus that employs the radiation detecting elements arranged in a two-dimensional pattern for detecting the irradiated radiation so as to acquires the digital image data representing the radiographic image captured.

The abovementioned radiographic image capturing apparatus has been widely known as the FPD (Flat Panel Detector), and framed as an exclusive-use type radiographic image capturing apparatus in which the FPD was integrally equipped into the supporting base (for instance, set forth in JP3639750, Japanese Patent Gazette). However, in recent years, a portable type radiographic image capturing apparatus, which accommodates the radiation detecting elements, etc. inside its housing so as to make it portable, has been developed and put into a practical use (for instance, set forth in Tokkai 2006-058124 and Tokkaihei 6-342099, both are Japanese Patent Application Laid-Open Publications).

Further, as the radiographic image capturing apparatus, there have been developed various kinds of apparatuses, including: the direct-type radiographic image capturing apparatus in which the detecting elements generates electric charges corresponding to the radiation amount of X-ray, etc. irradiated thereon, so as to directly convert the generated electric charges to the electric signals; an indirect type radiographic image capturing apparatus in which the scintillator or the like converts the irradiated radiation to an electromagnetic wave having another wavelength, such as a visible light, etc., and then, the photoelectric converting elements, such as photodiodes, etc., generates electric charges corresponding to the energy intensities of the electromagnetic wave irradiated thereon, so as to convert the electric charges to the electric signals; etc.

In this connection, hereinafter in the present specification, each of the terms of the "detecting elements" to be employed in the direct-type radiographic image capturing apparatus and the "photoelectric converting elements" to be employed in the indirect-type radiographic image capturing apparatus is defined as a term of "radiation detecting elements".

Further, in the radiographic image capturing apparatus, for instance as shown in FIG. 5 detailed later, a plurality of radiation detecting elements 7 is arranged in a two-dimensional pattern on a detecting section P, so as to form a two-dimensional detecting area thereon.

Incidentally, when the radiographic image capturing operation is conducted by employing such the radiographic image capturing apparatus as abovementioned, even if the same amount of radiation is irradiated onto each of the radiation detecting elements 7, values of data sets D, respectively read from the radiation detecting elements 7, are not necessary same as each other, since the sensitivities of the radiation detecting elements 7 are usually different from each other.

To overcome such the drawback, the, arithmetic calculation processing is applied to each of the data sets D, for instance, by multiplying the value of each of the data sets D by a gain correction value G, as indicated by Equation (1) shown in the following, so as to equalize the different values of the data sets D, read from every one of radiation detecting elements 7 when the same amount of radiation is irradiated onto each of the radiation detecting elements 7, at a uniform value (for instance, set forth in Tokkai 2010-112866, Japanese Patent Application Laid-Open Publication, etc.).

$$D^* = \log\{G \times (D - O)\} \quad (1)$$

In this connection, in Equation (1), "$D^*$" represents the final image data that is acquired by applying the image processing to the data sets D read from the radiation detecting elements 7. Further, "O" represents offset data sets included in the data sets D and caused by dark electric charges generated by the thermal excitations or the like due to heat generated by the radiation detecting elements 7 itself. Further, the offset data sets O are usually acquired every time when the radiographic image capturing operation is conducted.

Further, although, according to the Equation (1), only the well-known and general purpose image processing is to be applied to the data sets D, in practice, other than the gain correction and/or the offset correction processing abovementioned, the various kinds of image processing, such as a normalize processing, a gradation correction processing corresponding to the image capturing portion and conditions, etc., are applied to the data sets D in order to acquire the final image data $D^*$.

In order to acquire the final image data $D^*$ to be employed for diagnosing purpose by applying appropriate image processing to the data sets D read from the radiation detecting elements 7, correction data, such as the gain correction value G for each of data sets D, etc., is required in regard to every one of radiation detecting elements 7. In this connection, hereinafter, the correction data, such as the gain correction value G, etc., is generally represented by correction data sets "$\alpha$".

Further, generally speaking, based on the data sets D (and offset data sets O) that are acquired by uniformly irradiating a predetermined amount of radiation, serving as parallel light, onto a radiation incident surface R (refer to the schematic diagram shown in FIG. 1, detailed later) of a radiographic image capturing apparatus while avoiding the influence of the shading unevenness of the irradiated radiation amount, just before the radiographic image capturing apparatus is shipped from the manufacturing factory (in other words, at the time of the factory default setting operation), each of the correction data sets "$\alpha$" is established in regard to each of the radiation detecting elements 7, so that the values of the final image data $D^*$ calculated according to the Equation (1) are made to be same as each other allover the radiation detecting elements 7.

Conventionally, any one of various types of radiation sources is installed in the radiation image capturing room in which the radiographic image capturing apparatus is actually operated. Further, according to a certain type of radiation source, for instance, an amount of radiation to be irradiated onto the radiation incident surface R of the radiographic image capturing apparatus increases at a central portion of the radiation incident surface R, while decreases at a peripheral section of the radiation incident surface R. Still thither, even if the same radiation source is employed, the difference between the radiation amounts of the central portion and the peripheral section varies depending on the distance between the position at which the radiation source is fixed and that of the detecting device (subject under inspection).

Further, sometimes, the radiation irradiated from the radiation source would exhibit a shading unevenness (irradiation unevenness) inherent to the radiation source concerned. Accordingly, generally speaking, the radiation characteristic in relation to the radiographic image capturing apparatus differs for every radiation source installed into the radiation image capturing room.

Still further, conventionally, in such the establishment that has employed the screen/film method, the aforementioned difference between the radiation amount at the central portion and that at the peripheral section has resulted in the density difference on the finished film. Accordingly, there has been such a historical circumstance that the diagnosis resolution capability has been established on the premise that the finished film naturally includes such the density difference, as the result of the long year diagnosing history being inherent to every establishment. Therefore, it is hardly to say that the gain adjustment processing for cancelling the difference between the radiation amount at the central portion and that at the peripheral section, so as to make the radiation characteristic to be flat, is always appropriate.

Yet further, conventionally, in the establishment that employs the CR method, since factors of the shading unevenness reside in the radiation source, the phosphor plate and the reading device, respectively, in the case that the shading unevenness correction processing is implemented at the former stage before the output gradation processing is applied, it is necessary to implement a new normalization processing for the FPD use in this former stage, and therefore, it becomes necessary to introduce a new image processing apparatus.

Accordingly, generally speaking, when the radiographic image capturing apparatus is introduced into the radiation image capturing room, the correction data sets "α", respectively established for the radiation detecting elements 7 at the time of the factory default setting operation as aforementioned, are readjusted so as to fit to the actual operation to be conducted in every establishment (diagnosis resolution capability), corresponding to the radiation characteristic of the radiation source currently installed into the radiation image capturing room, the image processing conditions, etc.

In this connection, hereinafter, in order to distinguish the correction data sets, such as the gain correction value G, etc., which are to be newly established at the time when the radiographic image capturing apparatus concerned is introduced into the radiation image capturing room, from the correction data sets "α" established at the time of the factory default setting operation, the newly established correction data sets are represented by correction data sets "α*". Further, in order to clarify the difference between the correction data sets "α" and the correction data sets "α*", hereinafter, these are defined as first correction data sets "α" (also referred to as first α-correction data) and second correction data sets "α*" (also referred to as second α*-correction data), respectively.

In the above case, based on the data sets D that are acquired by irradiating the predetermined amount of radiation, in accordance with the radiation characteristic of the radiation source installed in the radiation image capturing room concerned, onto the radiation incident surface R of a radiographic image capturing apparatus, etc., each of the second correction data sets "α*" is newly established in regard to each of the radiation detecting elements 7, so that the values of the final image data D* calculated according to the Equation (1) are made to be same as each other allover the radiation detecting elements 7.

In other words, the first correction data sets "α" is to be employed for making the values of the final data sets D* same as each other allover the radiation detecting elements 7 when the radiation, serving as parallel light, is irradiated onto a radiation incident surface R at the time of the factory default setting operation, and is to be derived from the characteristics of the radiographic image capturing apparatus itself; such as a conversion efficiency in the radiation detecting elements 7 for converting the radiation to the electric charges, a reading characteristic of a reading electric circuit (not shown in the drawings), etc.

Conversely speaking, in order to acquire the first correction data sets "α" originated from the characteristics of the radiation detecting elements 7 itself; the radiation roughly formed as parallel light is irradiated onto the radiographic image capturing apparatus at the time of the factory default setting operation.

On the other hand, the second correction data sets "α*" is such correction data that is derived from the radiation characteristic of the radiation source currently installed into the radiation image capturing room, the image processing conditions, etc., in addition to the abovementioned characteristics being inherent to the radiographic image capturing apparatus.

Accordingly, with respect to the first correction data sets "α", one set of correction data is established for every one of the radiation detecting elements 7 of the radiographic image capturing apparatus, while, with respect to the second correction data sets "α", one set of correction data is established for every one of the radiation sources respectively installed into the radiation image capturing rooms provided in, for instance, a hospital, etc. As a result, a number of second correction data sets "α*" established for the radiographic image capturing apparatus concerned becomes equal to the number of radiation sources being capable of irradiating radiation onto the radiographic image capturing apparatus concerned.

Incidentally, under the circumstances as abovementioned, for instance, in such a case that the radiographic image capturing apparatus should be returned to the factory or the like to fix it, due to the fact that the radiographic image capturing apparatus installed into the radiation image capturing room has malfunctioned, or due to the other reason, it is preferable that another radiographic image capturing apparatus is temporarily provided as the replacement of the radiographic image capturing apparatus concerned during the fixing term thereof In the abovementioned case, although first correction data sets "β" (hereinafter, also referred to as first β3-correction data), such as the gain correction value G, etc., have been established in advance with respect to the other radiographic image capturing apparatus of the replacement use at the time of the factory default setting operation, when introducing the concerned apparatus of the replacement use into the radiation image capturing room, it is necessary to newly reestablish second correction data sets "β*" (hereinafter, also referred to as second β*-correction data) in order to make it in conformity with the radiation characteristic of the radiation source currently installed into the radiation image capturing room. In this connection, hereinafter, in order to distinguish the first correction data sets, etc. of the other radiographic image capturing apparatus of the replacement use from the first correction data sets "α", etc. of the original radiographic image capturing apparatus, the first correction data sets, etc. of the former is represented by the first correction data sets "β", etc.

If the other radiographic image capturing apparatus of the replacement use were continuously operated in the radiation image capturing room from now on, it would be acceptable for the radiation technologist or the like to established the second correction data sets "β*" thereof. However, in reality, it is very cumbersome work for the radiation technologist or the like to purposely established the second correction data sets "β*" of the other radiographic image capturing apparatus of the replacement use, which will be replaced again by the original radiographic image capturing apparatus. Further, when a plurality of radiation sources is respectively installed into a plurality of radiation image capturing rooms, it becomes very troublesome work for the radiation technologist or the like to establish the second correction data sets "β*" for each of the plurality of radiation sources.

On the other hand, as indicated by the schematic diagram shown in FIG. 7, in such a case that a radiation image capturing room Ra is coupled to a console C through a network N, for instance, it is assumed that the radiation technologist or the like declares that he will use a radiation image capturing room Ra1 and another radiation image capturing room Ra2 by operating a console C1 In this case, the console C1 is correlated with the radiation image capturing room Ra1 and the radiation image capturing room Ra2.

Then, during the time when the radiation image capturing operation is currently performed in the radiation image capturing room Ra1, for instance, even if the other radiation technologist or the like intends to conduct the setting operation of the second correction data sets "β*" in regard to the radiographic image capturing apparatus of the replacement use, there has arisen such a problem that, due to the busy status of the console C1 for performing the radiation image capturing operation, it is impossible for the concerned personnel to conduct the setting operation of the second correction data sets "β*" until the busy status of the console C1 is eliminated.

SUMMARY OF THE INVENTION

To overcome the abovementioned drawbacks in conventional radiographic image capturing systems, it is one of objects of the present invention to provide an radiographic image capturing system, in which it is possible to easily establish second β* -correction data in regard to the radiographic image capturing apparatus for replacement use, and which makes it possible for the radiologist or the like to conduct the operations for setting the second β*-correction data in regard to the radiographic image capturing apparatus for replacement use, even if a console is busy for conducting the image capturing operation.

Accordingly, at least one of the objects of the present invention can be attained by any one of the radiographic image capturing systems described as follows.

(1) According to a radiographic image capturing system reflecting an aspect of the present invention, the radiographic image capturing system, comprises: a radiographic image capturing apparatus that is provided with a plurality of radiation detecting elements arranged in a two dimensional pattern, so as to reads out each of electric charges, generated in each of the radiation detecting elements by irradiating radiation thereon, as image data; a radiation source to emit the radiation to be irradiated onto the radiographic image capturing apparatus; a cradle that is provided in an image capturing room; and a console to create a radiographic image based on the image data transmitted from the radiographic image capturing apparatus; wherein the cradle reads out first α-correction data, established at a time of factory default setting operation, and second α*-correction data, established corresponding to the radiation source currently residing in the image capturing room, from the radiographic image capturing apparatus, which is currently inserted into the cradle, so as to store the first α-correction data and the second α*-correction data therein; and wherein, when a radiographic image capturing apparatus for replacement use, serving as a replacement use apparatus for the radiographic image capturing apparatus, is inserted into the cradle, the cradle reads out first β-correction data, established at a time of factory default setting operation, from the radiographic image capturing apparatus for replacement use, and then, based on the first β-correction data read from the radiographic image capturing apparatus for replacement use, and the first α-correction data and second α*-correction data, both read from the radiographic image capturing apparatus, serving as an original apparatus, the cradle calculates second β*-correction data corresponding to the radiation source currently residing in the image capturing room, so as to establish the second β*-correction data above-calculated in regard to the radiographic image capturing apparatus for replacement use.

(2) According to another aspect of the present invention, in the radiographic image capturing system recited in item 1, when reading out the first α-correction data and the second α*-correction data from the radiographic image capturing apparatus currently inserted, the cradle also reads out identification information for identifying the radiographic image capturing apparatus serving as the original apparatus, so as to store the identification information, the first α-correction data and the second α*-correction data, therein, while correlating the identification information with the first α-correction data and the second α*-correction data; and wherein, when the radiographic image capturing apparatus for replacement use, serving as the replacement use apparatus for the radiographic image capturing apparatus serving as the original apparatus, is inserted into the cradle, and the identification information for identifying the radiographic image capturing apparatus serving as the original apparatus is inputted through a inputting device, the cradle calculates the second β*-correction data corresponding to the radiation source currently residing in the image capturing room, based on the first β-correction data in regard to the radiographic image capturing apparatus for replacement use, and the first α-correction data and the second α*-correction data read out from the radiographic image capturing apparatus serving as the original apparatus and designated by the identification information, so as to establish the second β*-correction data in regard to the radiographic image capturing apparatus for replacement use.

(3) According to still another aspect of the present invention, the radiographic image capturing system recited in item 1 or item 2, further comprises: a management apparatus that manages the first α-correction data and the second α*-correction data in regard to the radiographic image capturing apparatus serving as the original apparatus; wherein, when the radiographic image capturing apparatus for replacement use, serving as the replacement use apparatus for the radiographic image capturing apparatus serving as the original apparatus, is inserted into the cradle, instead of storing the first α-correction data and the second α*-correction data, in regard to the radiographic image capturing apparatus serving as the original apparatus, in its own, the cradle acquires the first α-correction data and the second α*-correction data from the management apparatus, and then, calculates the second β*-correction data so as to establish the second β*-correction data in regard to the radiographic image capturing apparatus for replacement use.

(4) According to still another aspect of the present invention, in the radiographic image capturing system recited in item 3, when reading out the first α-correction data and the second α*-correction data from the radiographic image capturing apparatus currently inserted, the cradle also reads out identification information for identifying the radiographic image capturing apparatus serving as the original apparatus, so as to transmit the identification information, the first α-correction data and the second α*-correction data, to the management apparatus, while correlating the identification information with the first α-correction data and the second α*-correction data; and, when the radiographic image capturing apparatus for replacement use, serving as the replacement use apparatus for the radiographic image capturing apparatus serving as the original apparatus, is inserted into the cradle, and the identification information for identifying the radiographic image capturing apparatus serving as the original apparatus is inputted through a inputting device, the cradle transmits the identification information to the management apparatus so as to acquire the first α-correction data and the second α*-correction data in regard to the radiographic image capturing apparatus serving as the original apparatus, and then, calculates the second β*-correction data in regard to the radiographic image capturing apparatus for replacement use, so as to establish the second β*-correction data for the radiographic image capturing apparatus for replacement use.

(5) According to still another aspect of the present invention, the radiographic image capturing system recited in any one of items 1-4, further comprises: a management apparatus that manages the first α-correction data and the second α*-correction data in regard to the radiographic image capturing apparatus serving as the original apparatus; wherein, when completing operations for calculating the second β*-correction data in regard to the radiographic image capturing apparatus for replacement use, the cradle transmits the first β-correction data, read from the radiographic image capturing apparatus for replacement use, and the second β*-correction data, in addition to identification information for identifying the radiographic image capturing apparatus for replacement use, to the management apparatus so as to make the management apparatus manage the first β-correction data and the second β*-correction data in regard to the radiographic image capturing apparatus for replacement use.

(6) According to still another aspect of the present invention, the radiographic image capturing system recited in any one of items 2-5, further comprises: a management apparatus that manages the first α-correction data and the second α*-correction data in regard to the radiographic image capturing apparatus serving as the original apparatus; wherein, when the radiographic image capturing apparatus for replacement use, serving as the replacement use apparatus for the radiographic image capturing apparatus serving as the original apparatus, is inserted into the cradle, the cradle reads out the first β-correction data from the radiographic image capturing apparatus for replacement use, and then, transmits the first β-correction data to the management apparatus, instead of calculating the second β*-correction data in regard to the radiographic image capturing apparatus for replacement use within the cradle; and wherein the management apparatus calculates the second β*-correction data in regard to the radiographic image capturing apparatus for replacement use, based on the first β-correction data transmitted from the cradle in regard to the radiographic image capturing apparatus for replacement use, and the first α-correction data and the second α*-correction data in regard to the radiographic image capturing apparatus serving as the original apparatus, so as to establish the second β*-correction data above-calculated in regard to the radiographic image capturing apparatus for replacement use, through the cradle.

(7) According to still another aspect of the present invention, in the radiographic image capturing system recited in item 6, when the radiographic image capturing apparatus for replacement use, serving as the replacement use apparatus for the radiographic image capturing apparatus serving as the original apparatus, is inserted into the cradle, and the identification information for identifying the radiographic image capturing apparatus serving as the original apparatus is inputted through a inputting device, the cradle transmits the first β-correction data, read from the management apparatus in regard to the radiographic image capturing apparatus for replacement use, and the identification information of the radiographic image capturing apparatus serving as the original apparatus; and the management apparatus calculates the second β*-correction data in regard to the radiographic image capturing apparatus for replacement use, based on the first β-correction data transmitted from the cradle in regard to the radiographic image capturing apparatus for replacement use, and the first α-correction data and the second α*-correction data transmitted from the cradle in regard to the radiographic image capturing apparatus serving as the original apparatus, which corresponds to the identification information, so as to establish the second β*-correction data above-calculated in regard to the radiographic image capturing apparatus for replacement use, through the cradle.

(8) According to yet another aspect of the present invention, the radiographic image capturing system recited in any one of items 1-7, further comprises: a management apparatus that manages the first α-correction data and the second α*-correction data in regard to the radiographic image capturing apparatus serving as the original apparatus; and a plurality of the radiation sources; wherein either the cradle or the management apparatus stores plural groups of the second α*-correction data, which respectively correspond to the radiation sources, in addition to the first α-correction data in regard to the radiographic image capturing apparatus serving as the original apparatus, therein.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 11 shows a schematic diagram indicating an example of image capturing order information;

FIG. 12 shows a schematic diagram indicating an example of a selection screen in which image capturing order information is displayed;

DETAILED DESCRIPTION OF THE PREFERRED EMBODIMENT

Figure 1:
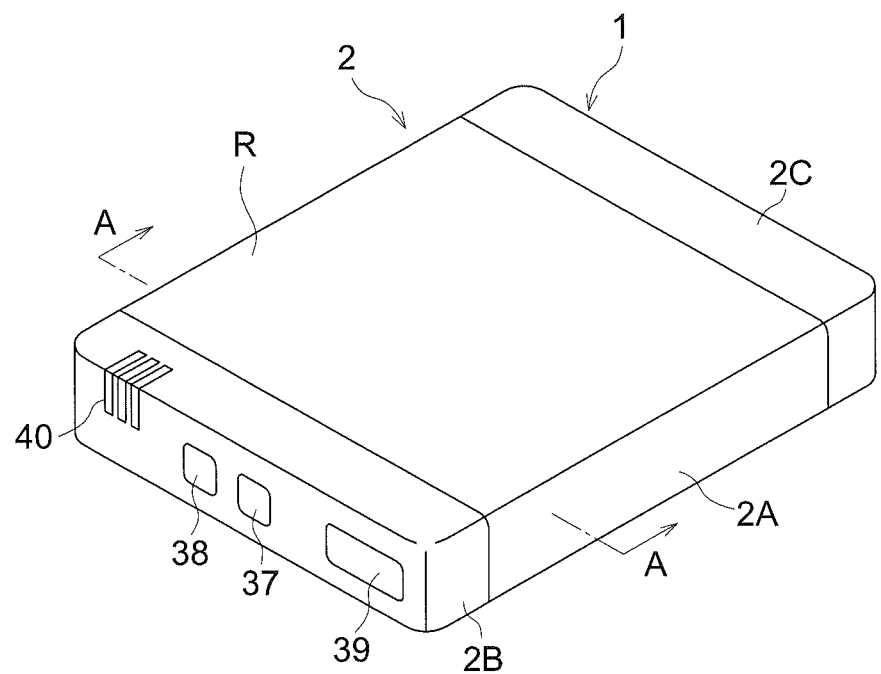
FIG. 1 shows a schematic diagram indicating a perspective view of an outer appearance of a radiographic image capturing apparatus, embodied in the present invention.

Referring to the drawings, the radiographic image capturing system, embodied in the present invention, will be detailed in the following. However, the scope of the present invention is not limited to the embodiment indicated by the drawings.

<With Respect to Radiographic Image Capturing Apparatus>

Initially, a radiographic image capturing apparatus 1 to be employed for a radiation image capturing operation performed in a radiographic image capturing system 50, embodied in the present invention, will be detailed in the following.

In this connection, hereinafter, an indirect-type radiographic image capturing apparatus that is provided with a scintillator, etc., to convert the emitted radiation to the electro-magnetic wave, such as visible light, etc., having a wavelength other than that of the emitted radiation, so as to acquire the electric signals therefrom, will be detailed in the following. However, it is needless to say that the present invention is also applicable for a direct-type radiographic image capturing apparatus that employs a radiation detecting element to directly detect the radiation without employing the scintillator or the like.

Figure 2:
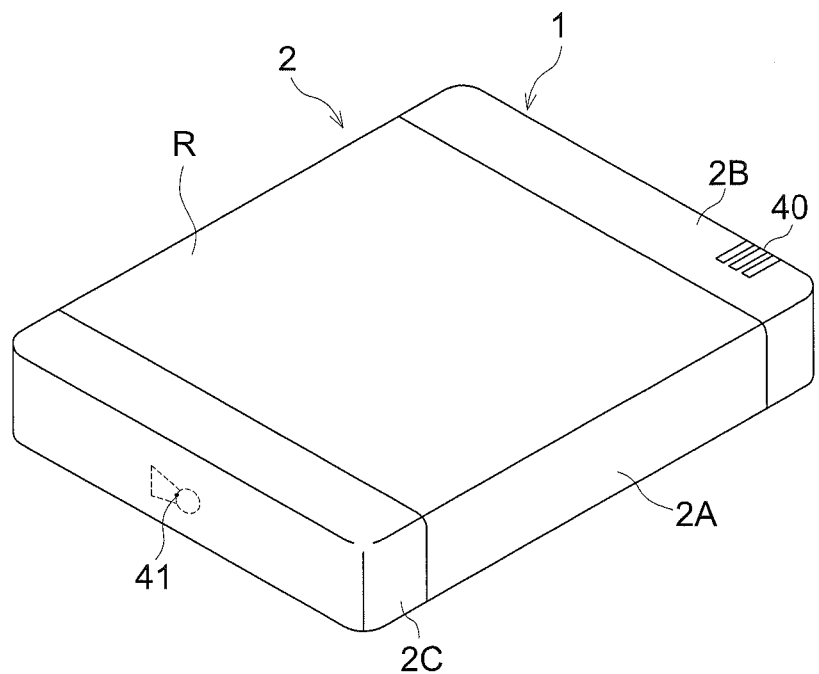
FIG. 2 shows a schematic diagram indicating a perspective view of another outer appearance of a radiographic image capturing apparatus same as that shown in FIG. 1, when viewing from a direction opposite to that of FIG. 1.
Figure 3:
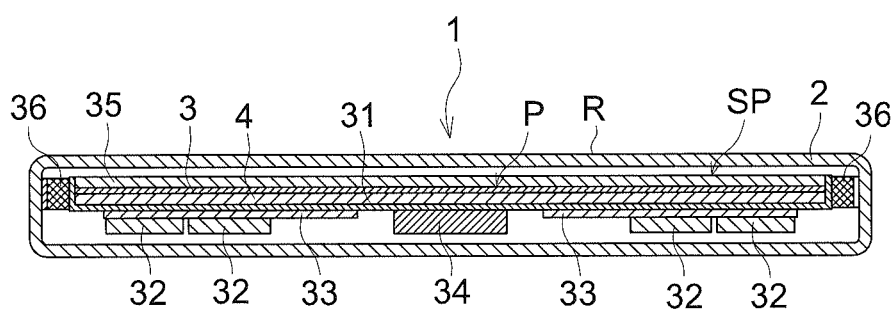
FIG. 3 shows a schematic diagram indicating a cross sectional configuration, cut along the A-A line indicated in the schematic diagram shown in FIG. 1.

FIG. 1 shows a schematic diagram indicating an outer appearance of the radiographic image capturing apparatus 1, while FIG. 2 shows a schematic diagram indicating another outer appearance of the radiographic image capturing apparatus 1, viewing from a direction opposite to that of FIG. 1. Further, FIG. 3 shows a schematic diagram indicating a cross sectional configuration, cut along the A-A line indicated in the schematic diagram shown in FIG. 1. As shown in FIG. 1 through FIG. 3, the radiographic image capturing apparatus 1 is provided with a housing 2 formed in a chassis shape, in which a scintillator 3 and a sensor panel SP constituted by a circuit board 4, etc., are accommodated.

As shown in FIG. 1 and FIG. 2, a housing main section 2A, which is a part of the housing 2 of the radiographic image capturing apparatus 1 and is shaped in a hollow rectangular cylinder having a radiation incident surface R, is made of a radiation permeable material, such as a carbon plate, a plastic material, etc. Further, the housing 2 is formed by covering both end portions of the housing main section 2A with a covering member 2B and a covering member 2C, respectively.

As shown in FIG. 1, a power switch 37, a selection switch 38, a connector 39, an indicator 40 that is constituted by LEDs (Light Emitting Diodes), etc., to display a buttery status, an operating status of the radiographic image capturing apparatus 1, etc., etc., are arranged on the covering member 2B disposed at one end portion of the housing 2.

Further, as shown in FIG. 2, an antenna section 41, which serves as a wireless communicating section to transmit wireless signals representing a cassette ID (IDentification), serving as identification information of the radiographic image capturing apparatus 1, to a management apparatus S, and to transfer image data sets D, etc., to a console C, detailed later, through a wireless communication link, is embedded into the covering member 2C disposed at the opposite side of the housing 2. In this connection, when the antenna section 41 is installed into the radiographic image capturing apparatus 1, a position at which the antenna section 41 is to be disposed on the housing 2 and a number of the antennas to be embedded are determined as needed.

Still further, in the present embodiment, the antenna section 41 is so constituted that the wireless LAN (Local Area Network), which is in conformity with the specification in the IEEE802.11 standard, is employed so as to make it possible to conduct the operation for communicating with the console C in the wireless communication mode through an access point 53 detailed later.

Yet further, as shown in FIG. 3, a substrate 31 is disposed at a lower side of a circuit board 4 of a sensor panel SP, while placing a thin lead plate or the like (not shown in the drawings) between them. A printed circuit board 33 on which electric parts 32, etc. are mounted, a buffer member 34, etc. are attached onto the substrate 31. In this connection, a glass base plate 35 is disposed on the radiation incident surface R side surface of a scintillator 3, so as to protect them. In addition, another buffer member 36 is inserted between the sensor panel SP and the side surface of the housing 2.

The scintillator 3 is to be laminated with the detecting section P, detailed later, of the circuit board 4. For instance, employed as the scintillator 3 in the radiographic image capturing apparatus 1 is such a scintillator that includes phosphor material as its main gradients, and is capable of converting the incident radiation, currently received, to the electro-magnetic wave having a wavelength in a range of 300-800 nm, namely, the electro-magnetic wave having the wavelength of the visible light as its center wavelength so as to output the converted electro-magnetic wave.

Figure 4:
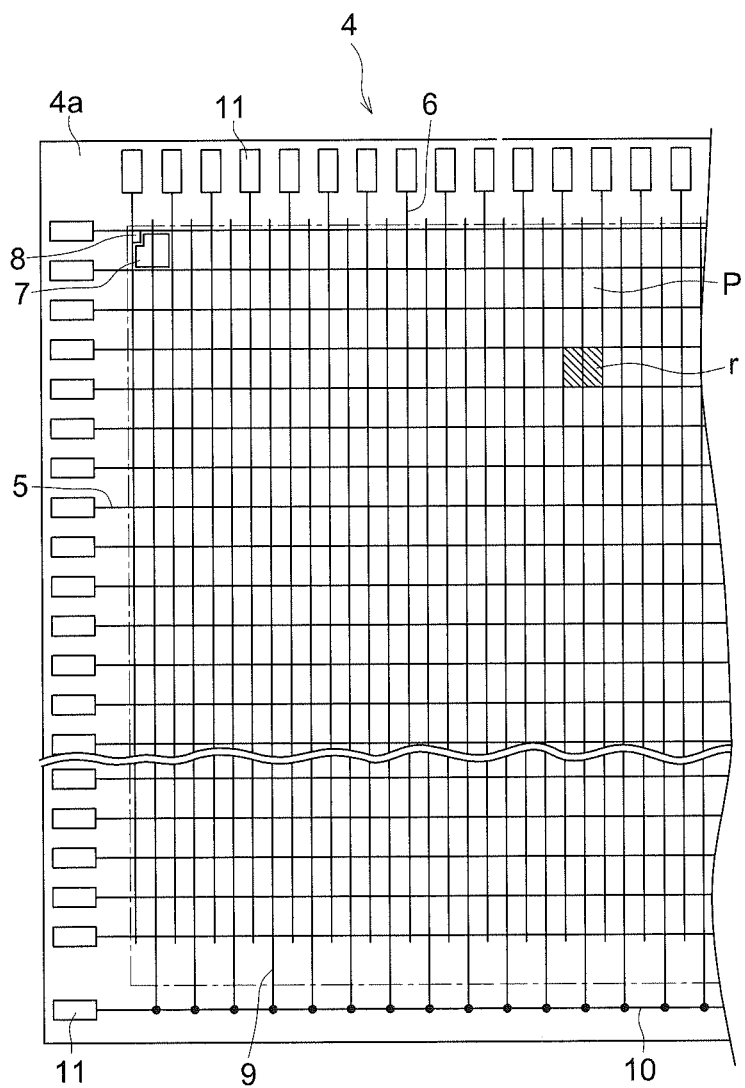
FIG. 4 shows a schematic diagram indicating a plane view of a layout pattern configuration of a circuit board installed in a radiographic image capturing apparatus, embodied in the present invention.

The circuit board 4 is constituted by a glass base plate, and as shown in FIG. 4, a plurality of scanning lines 5 and a plurality of signal lines 6 are arranged on a glass plate surface 4a opposing to the scintillator 3 of the circuit board 4, in such a manner that the scanning lines 5 and the signal lines 6 are intersect with each other. Each of the radiation detecting elements 7 is allotted onto each of small regions "r" sectioned by the plurality of scanning lines 5 and the plurality of signal lines 6 arranged on the glass plate surface 4a of the circuit board 4.

As described in the above, the whole area including all of the small regions "r", on which the radiation detecting elements 7, two-dimensionally and respectively arranged on the small regions "r" sectioned by the scanning lines 5 and the signal lines 6, are disposed, namely, the area surrounded by the alternate long and short dash lines as shown in FIG. 4, is defined as the detecting section P.

Although photodiode elements are employed as the radiation detecting elements 7 in the present embodiment, other than the above, it is also applicable that phototransistor elements are employed as the radiation detecting elements 7. As indicated in the enlarged schematic diagram shown in FIG. 5, each of the radiation detecting elements 7 is coupled to a source electrode 8s of a TFT 8 serving as a switching device. Further, a drain electrode 8d of the TFT 8 is coupled to corresponding one of the signal lines 6.

Further, when an ON voltage is applied onto a gate electrode 8g by a gate driver (not shown in the drawings) through corresponding one of the scanning lines 5, the TFT 8 is turned into an ON state so as to emit an electric charge, currently accumulated within corresponding one of the radiation detecting elements 7, to corresponding one of the signal lines 6. On the other hand, when an OFF voltage is applied onto the gate electrode 8g by the gate driver through corresponding one of the scanning lines 5, the TFT 8 is turned into an OFF state so as to halt the emission of the electric charge to corresponding one of the signal lines 6, and to maintain the electric charge within corresponding one of the radiation detecting elements 7.

Figure 5:
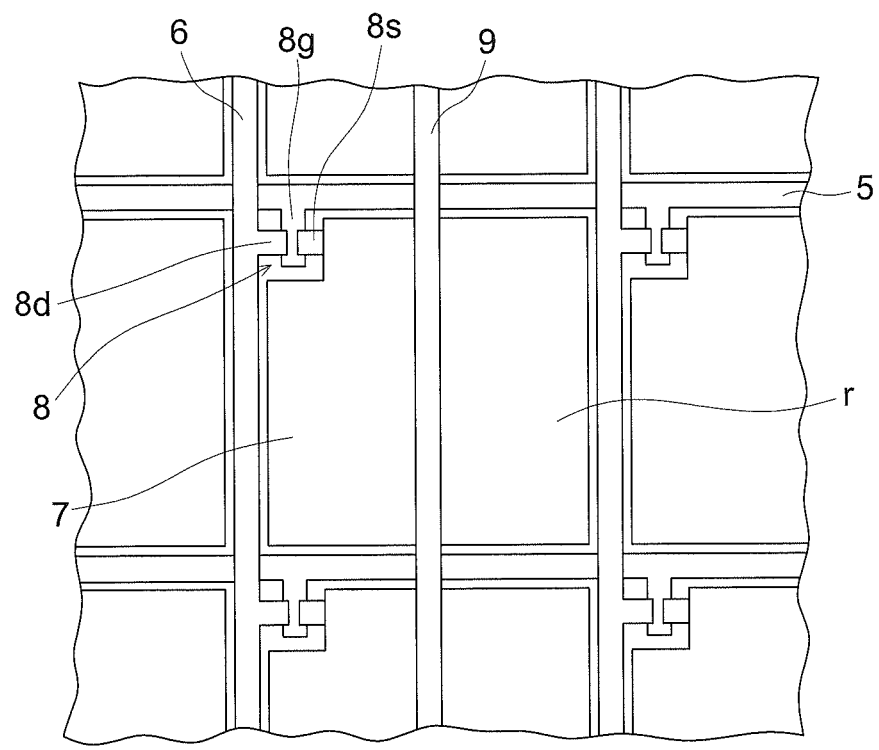
FIG. 5 shows an enlarged schematic diagram indicating a configuration of radiation detecting elements, TFTs (Thin Film Transistors), etc., which are fabricated on a small region of a circuit board shown in FIG. 4.

As shown in FIG. 4 and FIG. 5, bias lines 9 are respectively coupled to the radiation detecting elements 7 arranged in the column pattern, and the bias lines 9 are further coupled to a single connection line 10 at a position outside the detecting section P of the circuit board 4, so that a reverse bias voltage is applied to each of the radiation detecting elements 7 through corresponding one of the bias lines 9 by a bias voltage source (not shown in the drawings).

Figure 6:
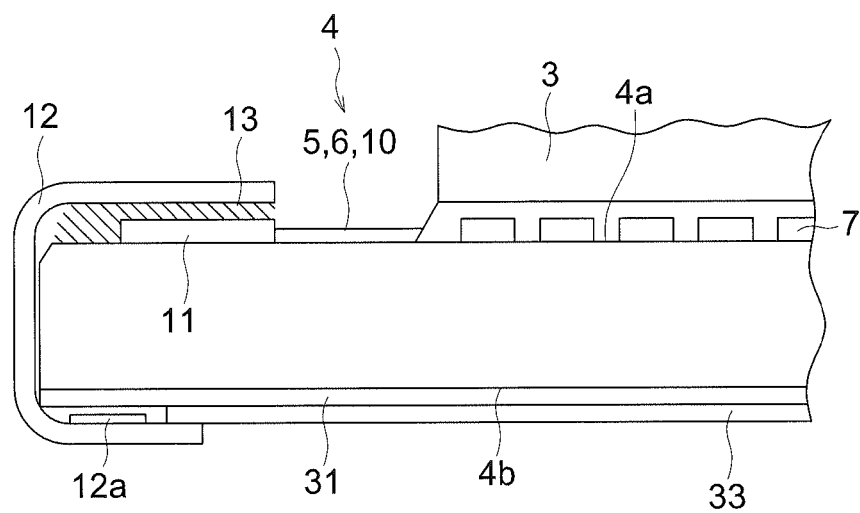
FIG. 6 shows a explanatory schematic diagram indicating a side view of a circuit board onto which a flexible electric circuit board, a PCB, etc., are mounted.

Further, the scanning lines 5, the signal lines 6 and the single connection line 10 of the bias lines 9 are respectively coupled to input/output terminals 11 (also referred to as pads 11) disposed at positions in the vicinity of peripheral edge portions of the circuit board 4. As shown in FIG. 6, a flexible electric circuit board 12 (also referred to as a Chip On Film), onto which chip-type parts, such as an IC (Integrated Circuit) 12a, etc., are mounted on a film, is connected to the input/output terminals 11 through an anisotropic conductive adhesive material 13, such as an anisotropic conductive film, an anisotropic conductive paste, etc.

Further, the flexible electric circuit board 12 is folded towards a reverse side surface 4b of the circuit board 4, so that the flexible electric circuit board 12 is connected to the printed circuit board 33 at the reverse side surface 4b. According to the abovementioned process, the circuit board 4 of the sensor panel SP to be installed in the radiographic image capturing apparatus 1 is formed. In this connection, depictions of the electric parts 32, etc. are omitted from the cross sectional schematic diagram shown in FIG. 6.

On the other hand, the radiographic image capturing apparatus 1 is so constituted that, after the radiation penetrated through the subject, such as a patient body, etc., has been irradiated onto the radiation incident surface R of the radiographic image capturing apparatus 1, the operations for respectively reading image data sets D from the radiation detecting elements 7 are implemented, and in the present embodiment, the radiographic image capturing apparatus 1 is so constituted that each of the image data sets D read from each of the radiation detecting elements 7 is thinned out by employing a predetermined thinning rate, to reduce a data amount of each of the image data sets D so as to create thinned-out image data sets Dt.

Successively, every time when completing the image capturing operation, the radiographic image capturing apparatus 1 transmits the thinned-out image data sets Dt to the console C, detailed later, through the antenna section 41 serving as the wireless communicating section. Successively, after transmitting the thinned-out image data sets Dt, the radiographic image capturing apparatus 1 automatically transmits the image data sets D, as well. In this connection, the cassette ID of the radiographic image capturing apparatus 1 concerned is attached to both the thinned-out image data sets Dt and the image data sets D to be transmitted to the console C.

In addition to the above, the radiographic image capturing apparatus 1 is so constituted that the radiographic image capturing apparatus 1 conducts a dark component read processing for acquiring an offset component caused by dark charge and superimposed onto each of the image data sets D at a predetermined timing, and calculates offset data sets O based on dark read values "d" acquired by performing the dark component read processing so as to automatically transmit the offset data sets O to the console C.

On the other hand, as aforementioned, with respect to the radiographic image capturing apparatus 1, the first correction data sets "α", such as the gain correction values G, etc., have been respectively established for the radiation detecting elements 7 at the time of the factory default setting operation, and information in regard to the first correction data sets "α", respectively corresponding to the radiation detecting elements 7, are stored in a storage section incorporated in the radiographic image capturing apparatus 1 concerned. In this connection, it is also applicable that other information in regard to positions of defect pixels is also stored in the storage section concerned.

Further, as aforementioned, at the time when the radiographic image capturing apparatus 1 is introduced (installed) into an image capturing room Ra, detailed later, of a hospital, etc., the second correction data sets "α*", respectively corresponding to the radiation detecting elements 7, are newly established so as to make them in conformity with a radiation source 52 currently installed in the image capturing room Ra. Accordingly, the second correction data sets "α*", respectively corresponding to the radiation detecting elements 7, are also stored in the storage section concerned.

In this connection, as indicated in the schematic diagram shown in FIG. 7, etc., described later, when a plurality of radiation sources 52 is installed into the radiographic image capturing system 50, plural groups of second correction data sets "α*", respectively corresponding to the plurality of radiation sources 52 concerned, are established and stored in the storage section concerned.

<With Respect to Radiographic Image Capturing System>

Next, a configuration, etc. of the radiographic image capturing system 50 will be detailed in the following. FIG. 7 shows a schematic diagram indicating an overall configuration of the radiographic image capturing system embodied in the present invention.

In this connection, although such a case that the radiographic image capturing system 50 is constituted by a plurality of image capturing rooms Ra (Ra1-Ra3) and a plurality of consoles C (C1, C2) will be detailed in the following, it is needless to say that the radiographic image capturing system 50 may be provided with a single set of the image capturing room Ra and/or a single set of the console C, as an applicable embodiment of the present invention.

Further, although such a case that the management apparatus S and the console C are separately installed into the radiographic image capturing system 50 will be detailed in the following, it is also applicable that the system is so constituted that either a single set of console C or any one of plural consoles C is also provided with functions of the management apparatus S.

In the radiographic image capturing system 50, embodied in the present invention, a plurality of image capturing rooms Ra and a plurality of consoles C are coupled to each other through a network N, such as a LAN (Local Area Network), etc., and the management apparatus S is also coupled to the network N. Further, various kinds of other necessary apparatuses, such as a computer, an external apparatus that records a radiation image onto an image recording medium, such as a film, etc., so as to output radiation image data therefrom, an HIS (Hospital Information System), an RIS (Radiology Information System), etc.

Figure 7:
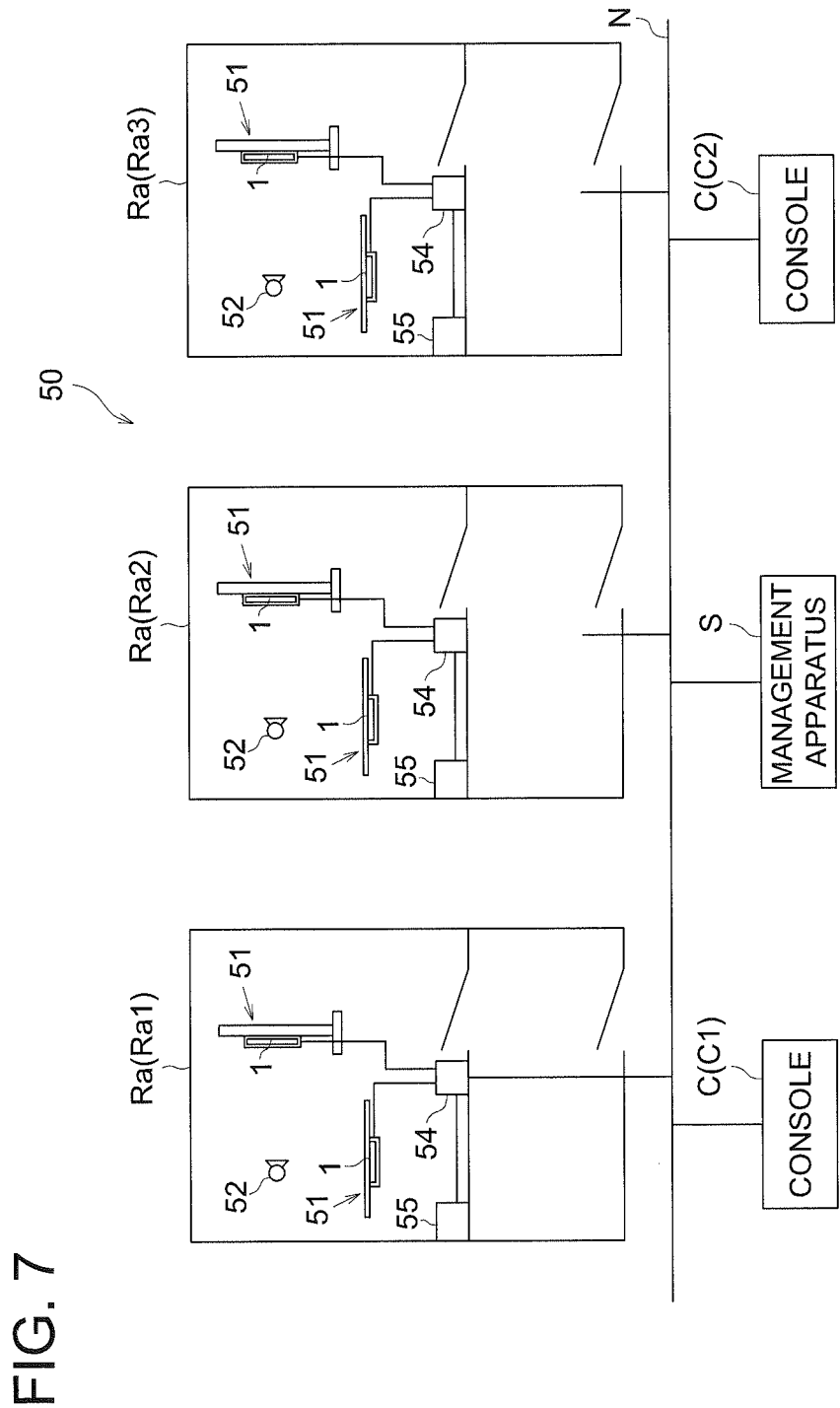
FIG. 7 shows a schematic diagram indicating an overall configuration of a radiographic image capturing system, embodied in the present invention.

Each of the image capturing rooms Ra (corresponding to each of the image capturing room Ra1, the image capturing mom Ra2 and the image capturing mom Ra3 indicated in the schematic diagram shown in FIG. 7) is used as such a mom in which the radiation image capturing operation is actually implemented by irradiating the radiation onto the subject being a part of the patient body (namely, an image capturing part of the patient concerned). The inner configuration of each of the image capturing rooms Ra, etc. in the radiographic image capturing system 50 will be detailed in the following.

Figure 8:
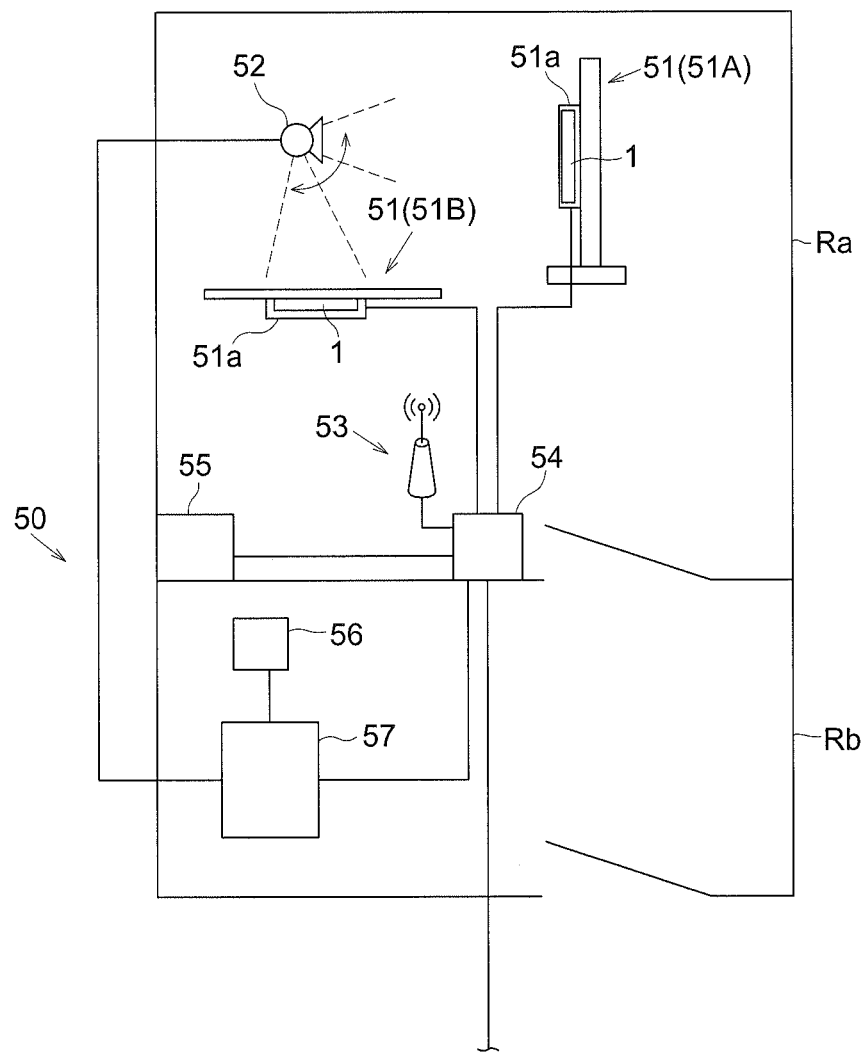
FIG. 8 shows a schematic diagram indicating an image capturing room, embodied in the present invention.

As shown in FIG. 8, a bucky 51, into which the radiographic image capturing apparatus 1 is loadable, is installed in the image capturing room Ra, so that the radiographic image capturing apparatus 1 can be loaded into a cassette holding section 51a (also referred to as a cassette holder 51a) to use the bucky 51.

In this connection, although such a case that both a table type bucky 51A to be used for capturing an upright position radiograph and another wall-stand type bucky 51B to be used for capturing a supine position radiograph are provided as the bucky 51 in the image capturing room Ra is illustrated in the schematic diagram shown in FIG. 8, it is also applicable that, for instance, only the table type bucky 51A or only the wall-stand type bucky 51B is installed in the image capturing room Ra.

In the present embodiment, the bucky 51 is so constituted that a conventional CR cassette is also loadable into the cassette holding section 51a so as to make it possible to employ the conventional CR cassette for the radiation image capturing operation, as well. Accordingly, the existing bucky table for the CR cassette use currently installed in the image capturing room Ra is employed in the present embodiment, as it is.

For the abovementioned purpose, the size of the radiographic image capturing apparatus 1 is set at such a value that is the same as that of the conventional CR cassette. In other words, the CR cassette is formed in the size of 14 inch×17 inch, etc., which is in conformity with the JIS (Japan Industrial Standard) in regard to the size of the conventional cassette for screen film use (corresponding to IEC 60406). Further, the thickness of the CR cassette is set at a value in a range of 15 mm+1 mm~15 mm−2 mm.

Accordingly, in order to make it possible to load the radiographic image capturing apparatus 1 into the bucky 51 into which the conventional CR cassette in conformity with the JIS size is loadable, the radiographic image capturing apparatus 1 is also formed in the size, which is in conformity with the JIS in regard to the size of the conventional cassette for screen film use.

In this connection, when the existing bucky table to be used for the screen/film cassette or the CR cassette is not employed, it is not necessary to employ the abovementioned size for forming the radiographic image capturing apparatus 1, but it is possible to form the radiographic image capturing apparatus 1 in an arbitral size or shape. However, on that occasion, it becomes necessary to install a new bucky table that make it possible to load the radiographic image capturing apparatus 1, the shape of which has been arbitrarily established, therein.

Figure 9:
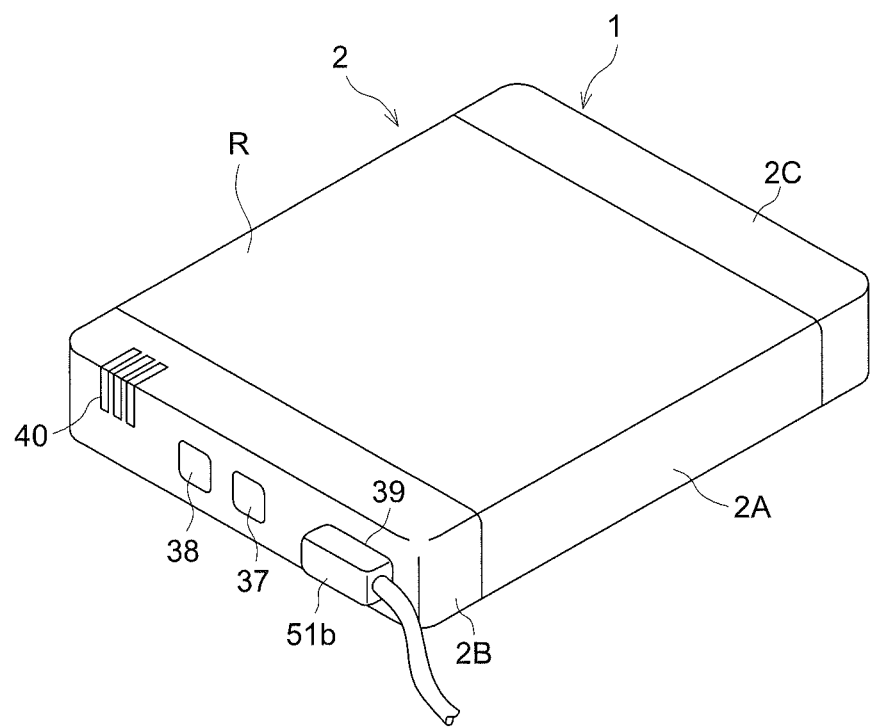
FIG. 9 shows a schematic diagram indicating a perspective view of an outer appearance of a radiographic image capturing apparatus, in such a state that a connector 39 of the radiographic image capturing apparatus and a connecting connector of a bucky table are coupled to each other.

Further, for instance, as shown in FIG. 9, it is also applicable that the system is so constituted that the radiographic image capturing apparatus 1 is loaded into the cassette holding section 51a in such a state that a connecting connector 51b attached to a leading end portion of the cable extended from the bucky 51 is coupled to the connector 39 serving as a recipient connector (refer to the schematic diagram shown in FIG. 1).

Figure 10:
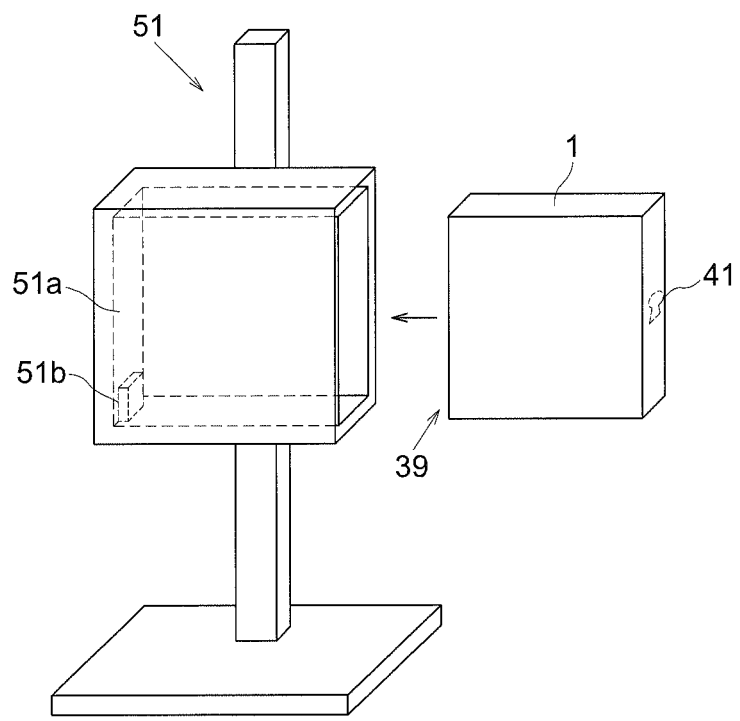
FIG. 10 shows an explanatory schematic diagram indicating a bucky table provided with a cassette holding section in which a connecting connector is provided.

Still further, for instance, as shown in FIG. 10, it is also applicable that the system is so constituted that the connecting connector 51b to be connected to the connector 39 of the radiographic image capturing apparatus 1 currently loaded, is provided in the inner section of the cassette holding section 51a, so that, when the radiographic image capturing apparatus 1 is loaded into the cassette holding section 51a, the connecting connector 51b of the bucky 51 and the connector 39 serving as the recipient connector of the radiographic image capturing apparatus 1 are automatically coupled to each other.

According to any one of the configurations shown in FIG. 9 and FIG. 10, since the connecting connector 51b of the bucky 51 and the connector 39 of the radiographic image capturing apparatus 1 are coupled to each other, it becomes possible to supply an electric power from the bucky 51 to the radiographic image capturing apparatus 1, and as a result, it becomes possible to prevent the buttery incorporated in the radiographic image capturing apparatus 1 from consuming the electric charge currently charged therein.

Still further, it is also applicable that the system is so constituted that, when transmitting the image data sets D to the console C, the radiographic image capturing apparatus 1, currently loaded into the bucky 51, transmits the image data sets D through the cable in the wired transmission mode by connecting the cable to a repeater 54 detailed later.

As shown in FIG. 7 and FIG. 8, at least a single set of radiation source 52 is provided in the image capturing room Ra.

Yet further, in the present embodiment, the radiation source 52 (refer to the schematic diagram shown in FIG. 8) is disposed at a position in the vicinity of the bucky 51, for instance, in such a manner that the radiation source 52 is hanged from the ceiling of the image capturing room Ra, and is activated in response to the instruction issued by console C at the time of implementing the radiation image capturing operation, so that a moving mechanism (not shown in the drawings) moves the radiation source 52 to a predetermined position. Then, by changing the radiation irradiating direction, it is possible to irradiate the radiation onto the radiographic image capturing apparatus 1 loaded into either the table type bucky 51A to be used for capturing the upright position radiograph, or the wall-stand type bucky 51B to be used for capturing the supine position radiograph.

The radiation source 52 is provided with an X-ray tube (not shown in the drawings). Receiving the tube excitation voltage and the tube current fed from a radiation generating device 57 detailed later, the X-ray tube irradiates a predetermined dose of radiation during a designated radiation-irradiating time interval.

Since the image capturing room Ra is electrically shielded by shielding members made of a lead material or the like, so as to prevent the radiation from being leaked out of the image capturing room Ra, even if the radiographic image capturing apparatus 1 tries to perform the operation for transmitting/receiving the information, such as the image data sets D, etc., through the antenna section 41 in the image capturing room Ra, it is difficult to perform the operation for transmitting/receiving the information as it is.

To overcome the abovementioned problem, as shown in FIG. 7 and FIG. 8, each of the image capturing rooms Ra is provided with the access point 53 that receives the image data sets D, etc., transmitted from the radiographic image capturing apparatus 1, and then, that transfers the concerned image data sets D, etc., to the console C. Further, the access point 53 is coupled to the repeater 54, and still further, is coupled to the console C and the management apparatus S through the repeater 54 and the network N (refer to FIG. 7).

In addition, the image capturing room Ra is provided with the repeater 54 that relays the bilateral communications between each of the apparatuses, installed in the image capturing room Ra and a front room Rb, and the network N located outside the image capturing room Ra. As shown in FIG. 8, other than the access point 53, various kinds of apparatuses, such as a cradle 55, the radiation generating device 57 installed in the front room Rb, etc., are coupled to the repeater 54, so as to relay the communications between each of the apparatuses and the console and the management apparatus S, located outside the image capturing room Ra, through the network N (refer to FIG. 7).

In the present embodiment, the cradle 55 is coupled to the repeater 54, so as to make it possible to conduct the processing for setting the second correction data sets "β*", in regard to a radiographic image capturing apparatus 1b for replacement use, through the cradle 55. The abovementioned processing will be detailed later on.

Figure 16:
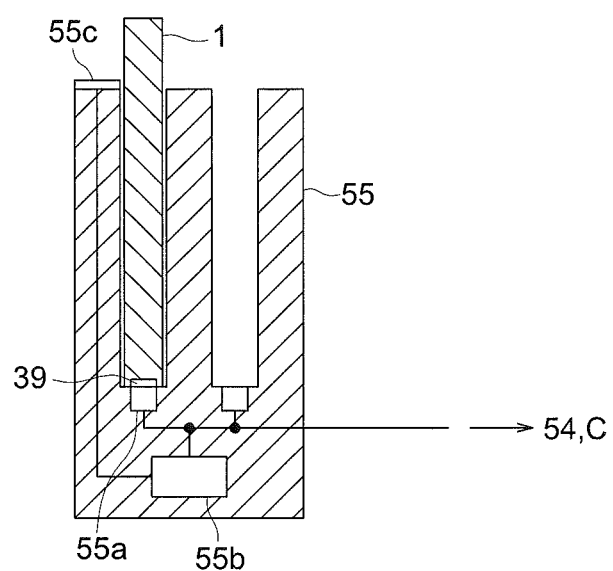
FIG. 16 shows a schematic diagram indicating a rough cross sectional view of a cradle, embodied in the present invention.

Further, for instance, as shown in FIG. 16 described later, the cradle 55 in the present embodiment is provided with an insertion opening into which the radiographic image capturing apparatus 1 is to be inserted. When the radiographic image capturing apparatus I brought into the image capturing room Ra is inserted into the insertion opening of the cradle 55, the connector 39 of the radiographic image capturing apparatus 1 and a connecting connector 55a of the cradle 55 are coupled to each other, so that the radiographic image capturing apparatus 1 can notify the console C of the cassette ID, serving as the identification information of the radiographic image capturing apparatus 1, through the cradle 55 and the repeater 54.

In this connection, since the cradle 55 is usually used for storing and/or charging the radiographic image capturing apparatus 1, etc., therein, it is also applicable in the present embodiment that the cradle 55 is also provided with the abovementioned functions, such as the storing function, the charging function, etc. Further, although the cradle 55 shown in FIG. 16, detailed later, is provided with two insertion openings into each of which the radiographic image capturing apparatus 1 is to be inserted, either a single insertion opening or more than three insertion openings is/are also applicable as the number of insertion openings to be provided in the cradle 55.

Further, the cradle 55 may be installed into either the image capturing room Ra or the front room Rb. When the cradle 55 is installed into the image capturing room Ra, the cradle 55 is disposed at such a position that is located at, for instance, a corner area of the image capturing room Ra, at which the radiation emitted by the radiation source 52 does not arrive.

As shown in FIG. 8, the radiation generating device 57 that is provided with a radiation exposure triggering switch 56 to be operated by a radiologist for instructing the radiation source 52 to commence the operation for irradiating the radiation onto the subject, etc. are installed in the front room Rb.

Then, in response to the instructions issued by the console C, the radiation generating device 57 supplies the predetermined tube excitation voltage and tube current to the radiation source 52, moves the radiation source 52 towards the predetermined position, changes the irradiating direction of the radiation source 52 and conducts other necessary operations so as to activate the radiation source 52.

Next, the console C and the management apparatus S, both coupled to the network N, other than the image capturing room Ra, will be detailed in the following. Initially, the management apparatus S will be detailed in the following.

The management apparatus S is constituted by a server computer in which a CPU (Central Processing Unit), a ROM (Read Only Memory), a RAM (Random Access Memory), an input/output interface, etc., (these are not shown in the drawings) are coupled to each other through a bus, etc. The ROM stores predetermined programs therein, so that the management apparatus S can read out a necessary program from the ROM, and then, develops the concerned program within the working area provided in the RAM so as to implement various kinds of processing by executing the developed program.

The present embodiment is so constituted that the management apparatus S acquires information indicating the residing place of each of the radiographic image capturing apparatuses 1, namely, one of image capturing rooms Ra in which the radiographic image capturing apparatus 1 concerned currently resides, so as to manage the information, etc. in regard to the image capturing room Ra in which the radiographic image capturing apparatus 1 concerned currently resides.

In addition to the above, the present embodiment is so constituted that the management apparatus S stores various kinds of information in regard to each of the radiographic image capturing apparatuses 1, including the first correction data sets "α", plural groups of the second correction data sets "α*" respectively corresponding to the radiation sources 52 installed in each of the image capturing rooms Ra, into a storage section (not shown in the drawings) so as to manage the information concerned. Further, it is applicable that the management apparatus S also stores other information in regard to the positions of defect pixels into the storage section so as to manage the other information concerned.

Then, receiving the information sent from the console C in regard to the image capturing room Ra in which the radiographic image capturing apparatus 1 concerned currently resides, the management apparatus S manages the received information in the manner as abovementioned, and at that time, transmits information in regard to the second correction data sets "α*" corresponding to the radiation source 52 in respect to the radiographic image capturing apparatus 1 concerned (or the second correction data sets "β*", in respect to the other radiographic image capturing apparatus 1 for replacement use, as detailed later), information in regard to the positions of defect pixels, etc., back to the console C concerned.

In this connection, as aforementioned, the first correction data sets "α", such as the gain correction values G respectively corresponding to the radiation detecting elements 7, etc., has been established for the radiographic image capturing apparatus 1 at the time of the factory default setting operation. Accordingly, at the time when the radiographic image capturing apparatus 1 concerned has been installed into the radiographic image capturing system 50 (namely, a hospital, etc., for which the radiographic image capturing system 50 is to be applied), the first correction data sets "α", respectively corresponding to the radiation detecting elements 7 and stored into the radiographic image capturing apparatus 1, are read out from the radiographic image capturing apparatus 1 concerned, and are transmitted to the management apparatus S in order to store them into the storage section while correlating the cassette ID, serving as the identification information of the radiographic image capturing apparatus 1, with the first correction data sets "α". In this connection, in such the case that the information in regard to the positions of defect pixels is transmitted, the concerned information in regard to the positions of defect pixels is also stored while correlating the cassette ID with the information concerned.

Further, during the initial installation period, the radiographic image capturing apparatus 1 concerned is brought into the image capturing room Ra1 in advance, and the radiation source 52 is made to irradiate radiation onto the radiographic image capturing apparatus 1 so as to read out the image data sets D from the radiation detecting elements 7, respectively. On the other hand, the offset data sets O are also read out in the state that no radiation is irradiated onto the radiographic image capturing apparatus 1 concerned. Then, for instance in the console C1, the second correction data sets "α*", such as the gain correction values G, etc., are established for the radiation detecting elements 7, respectively, in such a manner that, based on the image data sets D and the offset data sets O, above-readout, all of the values of the final image data sets D, calculated according to the Equation (1) aforementioned, are made to be the same in regard to allover the radiation detecting elements 7.

Successively, either a combination of the second correction data sets "α*" above-established and the identification information of the image capturing room Ra1, or another combination of the second correction data sets "α*" above-established and the identification information of the radiation source 52 concerned when plural radiation sources 52 have been installed in the image capturing room Ra1, is transmitted to the management apparatus S, so that the management apparatus S stores the received combination into the storage section while correlating it with the cassette ID. When the plural radiation sources 52 have been installed in the image capturing room Ra1, the abovementioned processing is conducted for every one of the plural radiation sources 52 concerned.

Still successively, the radiographic image capturing apparatus 1 concerned is sequentially brought into the image capturing room Ra2 and the image capturing room Ra3, and the abovementioned processing is implemented in each of them, so as to establish the plural groups of the second correction data sets "α*", respectively corresponding to the radiation sources 52 installed into the image capturing rooms Ra1 through Ra3, with respect to the radiographic image capturing apparatus 1 concerned. Then, the management apparatus S stores the plural groups of the second correction data sets "α*" above-established into the storage section, while correlating the cassette ID of the radiographic image capturing apparatus 1 concerned, the identification information of each of the radiation sources 52 (or the identification information of each of the image capturing rooms Ra when only a single radiation source 52 is installed in each of the image capturing rooms Ra) and each of the plural groups of the second correction data sets "α*" with each other, so as to manage them.

On the other hand, in the present embodiment, as detailed later, the cradle 55 and the management apparatus S calculates the second correction data sets "β*" and conducts the setting processing in regard to the radiographic image capturing apparatus 1 for replacement use. This processing will be detailed later on.

Yet successively, on that occasion, when the cradle 55 has calculated the second correction data sets "β*" and conducts the setting processing in regard to the radiographic image capturing apparatus 1 for replacement use, the cradle 55 transmits the first correction data sets "β" and the second correction data sets "β*" above-calculated in regard to the radiographic image capturing apparatus 1 for replacement use, in addition to the cassette ID serving as the identification information of the concerned radiographic image capturing apparatus 1 for replacement use, to the management apparatus S. Accordingly, receiving such the information abovementioned, the management apparatus S also stores the concerned information into the storage section to manage them.

Next, the console C (refer to the schematic diagram shown in FIG. 7) will be detailed in the following.

The console C is constituted by a computer in which a CPU (Central Processing Unit), a ROM (Read Only Memory), a RAM (Random Access Memory), an input/output interface, etc., (these are not shown in the drawings), are coupled to each other through a bus, etc. The ROM stores predetermined programs therein, so that the console C can read out a necessary program from the ROM, and then, develops the concerned program within the working area provided in the RAM so as to implement various kinds of processing by executing the developed program.

The console C is provided with a display section (not shown in the drawings) constituted by a CRT (Cathode Ray Tube), an LCD (Liquid Crystal Display), etc. Further, other than the above, various kinds of inputting devices, such as a keyboard, a mouse, etc., (not shown in the drawings) are coupled to the console C. Still further, a storage device (not shown in the drawings), constituted by a HDD (Hard Disc Drive), etc., is coupled to the console C or is incorporated in the console C.

The console C is so constituted that the image capturing operator, such as a radiologist or the like, can designated the image capturing room Ra to be employed for the image capturing operation. Based on the designation made by the operator concerned, the console C is correlated to the image capturing room Ra, and the console C declares against the other consoles C that the console C concerned currently employs the image capturing room Ra concerned, for the radiation image capturing operation.

Concretely speaking, for instance, once the operator of the console C1 designates the image capturing room Ra1 and the image capturing room Ra2, after that, it becomes impossible for the other console C2 to designate the image capturing room Ra1 and the image capturing room Ra2 until the designation made by the console C1 is released. As a result, for instance, it becomes impossible to transmit the image data sets D, etc. to the console C2 from the image capturing room Ra2. In this connection, according to the present embodiment, even if the console C has designated a specific image capturing room Ra, it is possible to transmit data, information, etc. to the management apparatus S from the designated image capturing room Ra.

Further, as indicated in the schematic diagrams shown in FIG. 7, FIG. 8, etc., the present embodiment is so constituted that, when each of the apparatuses installed in the image capturing room Ra and the front room Rb transmits signals, data, etc. to the console C, etc., all of the signals, data, etc. are transmitted through the relaying operation of the repeater 54. Further, since the repeater 54 attaches a repeater ID of its own to the signals, data, etc. currently transmitted during the relaying operation, the console C can recognize the image capturing room Ra from which the concerned signals, data, etc. have been transmitted, by referring to the repeater ID.

For this purpose, the present embodiment is so constituted that the console C is provided with a table in which identification information of the image capturing room Ra and the repeater ID of repeater 54 installed in the image capturing room Ra concerned are correlated with each other, so that, receiving the signals, data, etc., the console C can recognize the specific image capturing room Ra from which the signals, data, etc. concerned are transmitted, by referring to the repeater ID attached thereto.

Accordingly, when the console C is correlated with the image capturing room Ra by designating the image capturing room Ra concerned, as abovementioned, it becomes possible to securely transmit thinned data sets Dt, the image data sets D, etc., which have been transmitted from the radiographic image capturing apparatus 1 located within the image capturing room Ra concerned, to the console C concerned.

Still further, the present embodiment is so constituted that, when the cassette ID, etc. of the radiographic image capturing apparatus 1, which was brought into the image capturing room Ra and has been inserted into the cradle 55, is transmitted to the console C through the cradle 55 and the repeater 54, as aforementioned, the console C stores the concerned cassette ID into the storage section while correlating the concerned cassette ID with the identification information of the image capturing room Ra, so that the console C can recognize the fact that the radiographic image capturing apparatus 1 having the concerned cassette ID actually resides in the image capturing room Ra, to conduct the managing operation.

Still further, at the same time as abovementioned, the console C transmits both the cassette ID, serving as identification information of the radiographic image capturing apparatus 1, and the identification information of the image capturing room Ra to the management apparatus S, in order to notify the management apparatus S of the fact that the radiographic image capturing apparatus 1 having the concerned cassette ID actually resides in the image capturing room Ra.

Incidentally herein, before describing calculating operations, setting processing, etc. of the second correction data sets "β*" in regard to the radiographic image capturing apparatus 1 of replacement use, the image processing operations, etc. to be conducted in the console C will be detailed in the following, Under the operations to be conducted by the image capturing operator, the console C acquires necessary information, such as image capturing order information, etc., from the HIS or the RIS (not shown in the drawings) coupled to the network N.

The image capturing order information is established by designating at least a combination of an image capturing portion and an image capturing condition. Concretely speaking, the image capturing order information is constituted by patient information including a "patient ID" P2, a "patient name" P3, a "patient sex" P4, a "patient age" P5, a "diagnosis and treatment department" P6 and an "image capturing portion" P7; an "image capturing direction" P8, serving as an image capturing condition; a "bucky table ID" representing the bucky 51 to be employed; a "cassette ID" P10 of the cassette to be employed; etc. Then, an "image capturing order ID" P1 is automatically allotted to each of the image capturing order information in order of registering the image capturing request.

Acquiring the image capturing order information, the console C displays a selection screen H1, serving as a list view of the image capturing order information as shown in FIG. 12, onto the display section. According to the present embodiment, a image-capturing order information table h11, a selection button h12, a determining button 13 and a returning button h14 are displayed on the selection screen H1.

Figure 13:
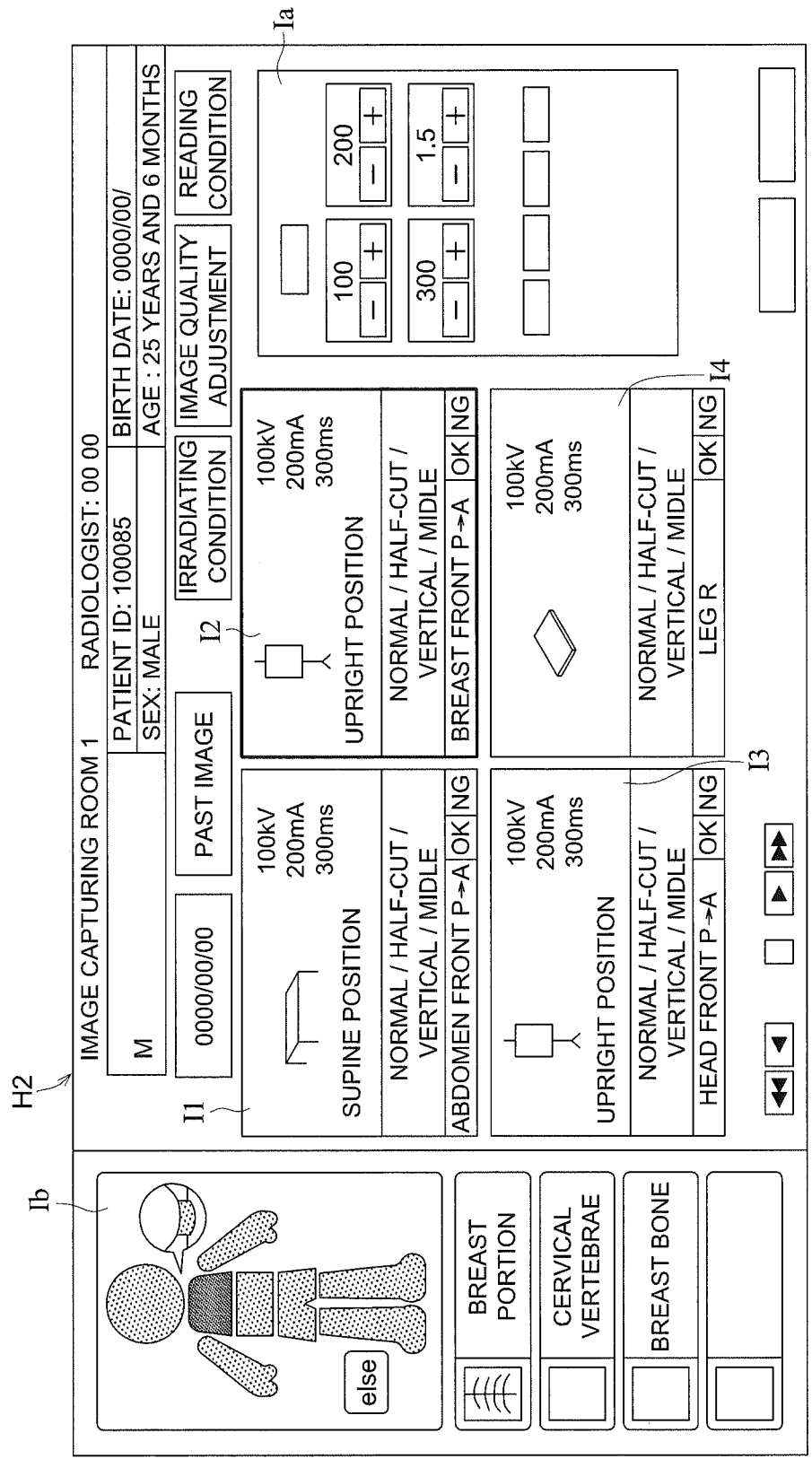
FIG. 13 shows a schematic diagram indicating an exemplified screen in which various kinds of icons or the like, corresponding to image capturing order information currently selected, are displayed.

Then, for instance, when the image capturing operator clicks the selection button h12 to select one of the image capturing order information, and then, clicks the determining button 13, the console C displays a detailed screen H2 onto the display section, as shown in FIG. 13.

As indicated in the schematic diagram shown in FIG. 13, icons I, respectively corresponding to each of the image capturing order information, are displayed on the detailed screen H2. Further, a pair of an "OK" button and a "NG" button is displayed on the lower section of each of the icons I. As detailed later, the image capturing operator clicks the "OK" button in such a case that the image capturing operator determines that the retaking operation is unnecessary when viewing a print preview image "p_pre" displayed at a position of an icon I, or in such a case that the image capturing operator determines that an radiation image "p" displayed at a position of an icon I is normal and intends to fix the radiation image "p" as it is. On the other hand, the image capturing operator clicks the "NG" button in such a case that the retaking operation is necessary and intends to reapply the image processing operation or the like to the radiation image "p".

Further, by clicking either a "+" button or a "−" button indicated on each of the items displayed within an area of a irradiating condition setting icon Ia located at the right side section of the detailed screen H2, it is possible for the image capturing operator to change the setting values of various kinds of radiation irradiating conditions, including the tube excitation voltage, the tube current, etc., of the radiation source 52 of the radiation generating device 57.

On the other hand, according to the present embodiment, the console C is so constituted that any one of the icons I including icons I1 through I4 is displayed in focus (icon I2, in the schematic diagram shown in FIG. 13) so as to make it distinguishable from the other icons, and the image capturing operation is conducted on the basis of the image capturing order information corresponding to the icon I currently displayed in focus. In this connection, when the image capturing operator intends to conduct another image capturing operation based on another image capturing order information, by clicking another icon I corresponding to the other image capturing order information, it is possible to easily shift the currently focused icon I to the other icon desired by the operator concerned.

Further, according to the present embodiment, in order to conduct the image capturing operation based on the image capturing order information corresponding to the currently focused icon I, the radiation generating device 57, installed in the image capturing room Ra, is controlled so as to activate the radiation source 52 according to the irradiation conditions, including a predetermined tube excitation voltage and tube current, a irradiation duration time, etc., and to change the irradiating direction thereof.

In this connection, the image capturing portion, corresponding to the currently focused icon I and designated by the image capturing order information, is indicated on the human body model displayed at a left side section of the detailed screen H2 in such a manner that the image capturing operator can recognize it at a glance.

On the other hand, after the radiation image capturing operation, based on the image capturing order information corresponding to the currently focused icon I, has been completed, the radiographic image capturing apparatus 1 transmits the thinned-out image data sets Dt, created from the image data sets D respectively corresponding to the radiation detecting elements 7, to the console C, as aforementioned. Receiving the thinned-out image data sets Dt sent from the radiographic image capturing apparatus 1, the console C displays the print preview image, based on the thinned-out image data sets Dt above-received, at the position at which the currently focused icon I has been displayed.

In this connection, it is also applicable that, in order to make it possible for the image capturing operator to easily view the print preview image "p_pre", the console C is so constituted that the print preview image "p_pre" is made to be enlarged so as to display the enlarged print preview image thereof on the detailed screen H2.

Successively after abovementioned, receiving the image data sets D sent from the radiographic image capturing apparatus 1 later on, the console C refers the cassette ID of the radiographic image capturing apparatus 1 concerned and the repeater ID of the repeater 54, both attached to the image data sets D, so as to confirm that the sender of the image data sets D is the specific radiographic image capturing apparatus 1 designated by the image capturing order information corresponding to the currently focused icon I, and then, correlates the image capturing order information with the image data sets D concerned.

Still successively, unless the image capturing operator, who has viewed the print preview image "p_pre", clicks the "NG" button during the predetermined duration time in which the print preview image "p_pre" is displayed on the detailed screen H2, the console C sifts the position of the currently focused icon I from the current position to another position of for instance, the icon I3, and, at the same time, commences the processing for creating the radiation image "p" based on the image data sets D acquired in the image capturing operation corresponding to the previously focused icon I2 and sent from the radiographic image capturing apparatus I concerned.

In this connection, when the image capturing operator, who has viewed the print preview image "p_pre", clicks the "NG" button during the predetermined duration time, abovementioned, the console C releases (deactivates) the operation for correlating the image capturing order information with the image data sets D, and at the same time, deletes the thinned-out image data sets Dt and the image data sets D. Further, the console C deactivates the processing for creating the radiation image "p" based on the image data sets D, etc.

As detailed later, the console C has acquired in advance the correction data in regard to the radiographic image capturing apparatus 1 actually employed for the image capturing operation, namely, the correction data sets "α", such as the gain correction values G aforementioned, etc., from the management apparatus S. In addition, as aforementioned, the radiographic image capturing apparatus 1 transmits the offset data sets O to the console C.

Accordingly, in the processing for creating the radiation image "p", the console C applies various kinds of processing, including the offset correction processing, the gain correction processing, the defect pixel compensation processing, the gradation correction processing corresponding to the image capturing portion, etc., to the image data sets D. Further, since, sometimes, the image capturing operation would be conducted by attaching a grid to the radiographic image capturing apparatus 1, the console C is so constituted that the filtering processing for removing a moire fringes caused by the grid is further applied to the image data sets D.

When the grid is employed for the image capturing operation, sometimes, a moire component might be generated in the image data sets D, depending on the relationship between the grid pitch and the pixel size of the radiographic image capturing apparatus 1. As the countermeasure set forth in Tokkai 2000-316126 (Japanese Patent Application Laid-Open Publication) against the abovementioned moire effect, by appropriately selecting the grid to be employed, it is possible to avoid the generation of the moire component. Further, as set forth in Tokkaihei 8-88765 (Japanese Patent Application Laid-Open Publication), it has been well-known that, after the image capturing operation is implemented by employing a grid at hand, the filtering processing, serving as the next process, is applied to the image data sets D, currently including the moire component, so as to eliminate the moire component thereof.

Since the radiographic image capturing apparatus 1 is used in the plurality of image capturing rooms Ra, as described in the present embodiment, or is used in a visited site as described in an embodiment detailed later, it is not a good idea to limit the kind of the grid to be employed to a certain range. In other words, it is preferable that the grid, which has been employed at the time when the image capturing operation is implemented by employing the CR cassette, is used as it is. Further, although it is possible to store grid pitch information of the grid that was actually employed for each of the image capturing operations while correlating the grid pitch information with the read image, for every time when implementing the image capturing operation, unlike in the case of the exclusive-type radiographic image capturing apparatus, the radiographic image capturing apparatus 1 requires a large scale repairing work for reforming the existing image capturing installations in order to make it possible to correlate the grid pitch information with the read image. Therefore, such the approach as abovementioned is not realistic.

Accordingly, it is preferable for the radiographic image capturing apparatus 1 such a method that several kinds of moire elimination filters, respectively corresponding to the grid pitches having availability for the practical image capturing operation, are provided in advance without limiting the grid to be used, and all of the filters provided in advance are sequentially applied to the image data sets D so as to acquire the radiation image "p" having no moire component.

Figure 14:
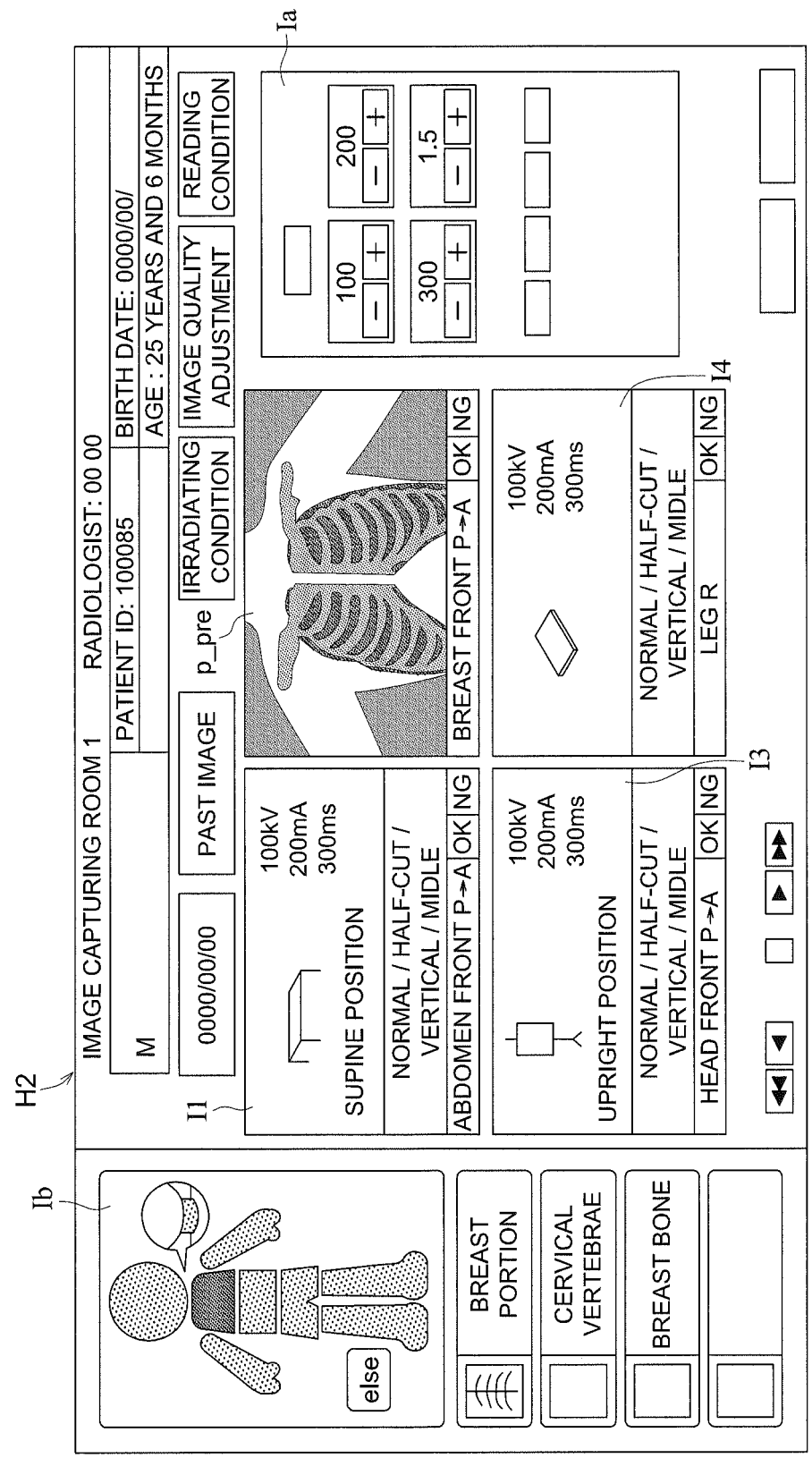
FIG. 14 shows a schematic diagram indicating another exemplified screen in which a preview image is displayed at a position of an original icon currently focused.
Figure 15:
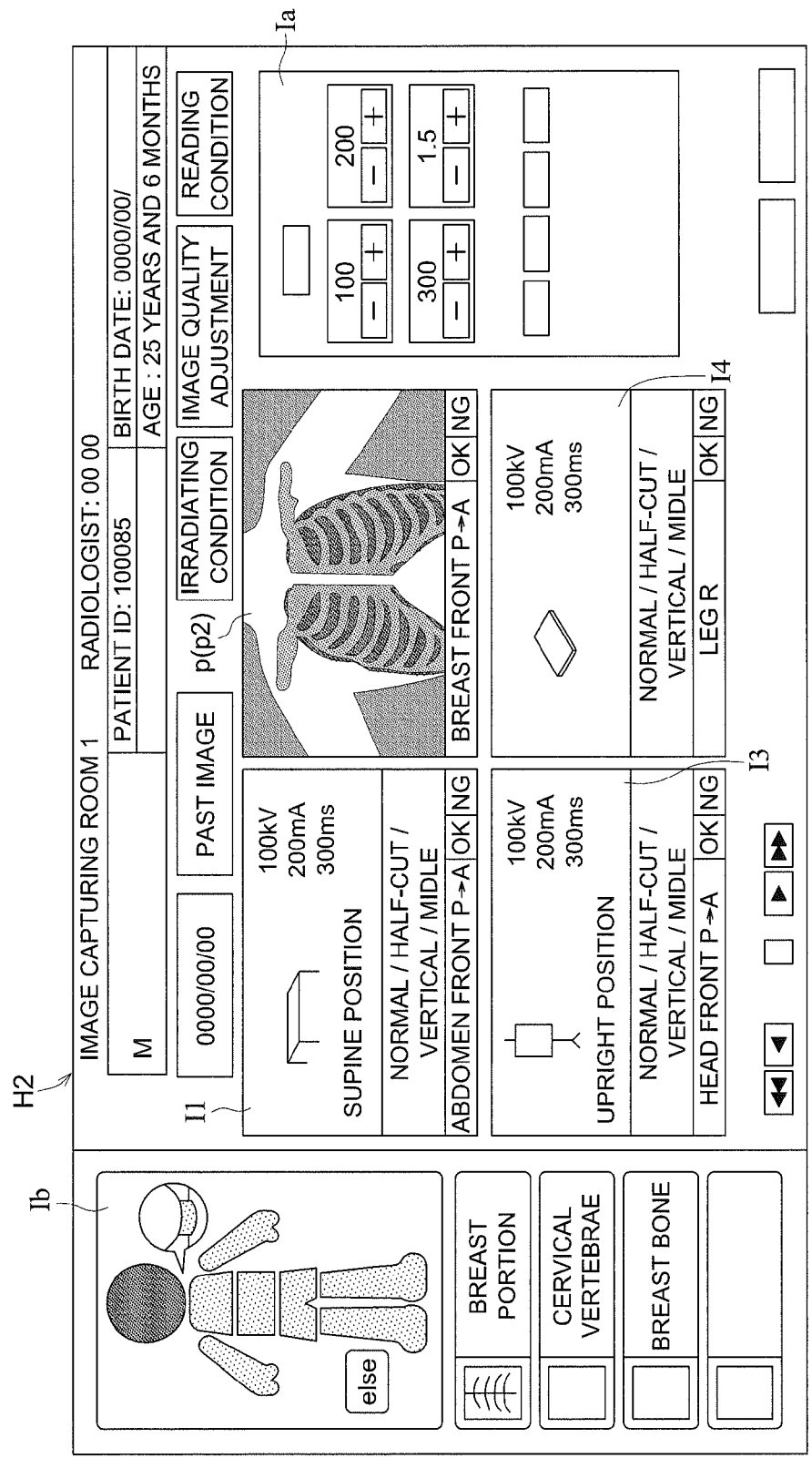
FIG. 15 shows a schematic diagram indicating still another exemplified screen in which a next icon is focused and a radiographic image is displayed at a position of an original icon.

As shown in FIG. 14, creating the radiation image "p", the console C display the print preview image "p_pre" at the original position of the icon I2. When the image capturing operator who viewed the print preview image "p_pre" determines that the radiation image "p" above-created is normal and clicks the "OK" button, the console C fixes the radiation image "p" and correlates the radiation image "p" with the image capturing order information concerned.

As described in the foregoing, according to the radiographic image capturing system 50 embodied in the present invention, the image capturing room Ra to be employed for the image capturing operation is designated from the console C (for instance, console C1), and then, when the radiographic image capturing apparatus 1 is brought into the image capturing room Ra designated in the above (for instance, image capturing room Ra1) and is inserted into the cradle 55, the cassette ID, etc. of the radiographic image capturing apparatus 1 are transmitted from the cradle 55 to the console C.

Successively, receiving the identification information of the cassette ID of the radiographic image capturing apparatus 1 and the image capturing room Ra concerned transmitted from the console C, the management apparatus S recognizes that the radiographic image capturing apparatus 1 concerned currently resides in the image capturing room Ra and commences the managing operations thereof, and at the same time, the information, including the second correction data sets "α*", etc. in regard to the radiographic image capturing apparatus 1 concerned, is transmitted to the console C concerned.

Still successively, receiving the image data sets D acquired by the image capturing operation implemented in the image capturing room Ra designated (for instance, image capturing room Ra1) while employing the radiographic image capturing apparatus 1 concerned and transmitted through the repeater 54, etc., the console C employs the second correction data sets "α*", etc., in regard to the radiographic image capturing apparatus I concerned, for applying the various kinds of image processing including the correction processing and the gradation processing to the image data sets D, so as to create the radiation image "p" for diagnosis use.

<With Respect to Processing when Introduction Radiographic Image Capturing Apparatus for Replacement Use>

Next, the processing to be conducted at the time when the radiographic image capturing apparatus 1 for replacement use is introduced into the radiographic image capturing system 50 configured as aforementioned, will be detailed in the following. In addition, associating with the above, the operations of the radiographic image capturing system 50 embodied in the present invention will be detailed in the following.

As described in the foregoing, due to a malfunction or the like of the radiographic image capturing apparatus 1, which has been installed into the radiographic image capturing system 50 through the processes aforementioned, (hereinafter, referred to as a radiographic image capturing apparatus 1a for discriminating it from a radiographic image capturing apparatus for replacement use), there has been such a possibility that it is necessary to bring the radiographic image capturing apparatus 1a back to the factory or the like in order to repair it.

In such a case as abovementioned, it is preferable that another radiographic image capturing apparatus 1b is temporarily provided as the replacement of the radiographic image capturing apparatus 1a concerned during the term of repairing the radiographic image capturing apparatus 1a concerned. However, in reality, it becomes very cumbersome and troublesome for the radiation technologist to conduct the abovementioned consecutive works even for the radiographic image capturing apparatus 1b, including sequentially bringing the radiographic image capturing apparatus 1b into each of the image capturing rooms Ra1 through Ra3 so as to irradiate the radiation emitted from corresponding one of the radiation sources 52 onto the radiographic image capturing apparatus 1b, and calculating the second correction data sets corresponding to each of the radiation sources 52 so as to establish it with respect to each of the radiation sources 52, as described in the foregoing.

In this connection, hereinafter, in contrast to the first correction data sets "α" and the second correction data sets "α*" of the radiographic image capturing apparatus 1a, serving as the original apparatus, the first correction data sets and the second correction data sets for the radiographic image capturing apparatus 1b, serving as the apparatus for replacement use, are referred to as first correction data sets "β" and second correction data sets "β*".

Further, as aforementioned, after the console C1 (refer to the schematic diagram shown in FIG. 7) has designated the image capturing room Ra1 and the image capturing room Ra2, there has arisen such a problem that, for instance, even if the radiologist intends to conduct the operations for calculating and setting the second correction data sets "β*" of the radiographic image capturing apparatus 1b for replacement use in the image capturing room Ra2, which is currently unused, as abovementioned, it is impossible for the radiologist to conduct the abovementioned operations for calculating and setting the second correction data sets "β*", since the console C1 is currently busy for implementing the image capturing operation, and it is impossible to transmit the image data sets D, etc. from the radiographic image capturing apparatus 1b for replacement use to the console C2.

To overcome such the problem as abovementioned, the present embodiment is so constituted that the cradle 55 and the management apparatus S are employed for making it possible not only to conduct the operations for calculating and setting the second correction data sets "β*" in regard to the radiographic image capturing apparatus 1b for replacement use in the image capturing room Ra2 currently designated by the console C1, but also to easily achieve the calculating and setting operations concerned.

Several patterns that make the abovementioned feature of the present invention possible will be detailed in the following.

<Pattern 1>

The pattern 1 in which the cradle 55 conducts all of the operations for calculating and setting the second correction data sets "β*" will be detailed in this item of "PATTERN 1".

In this case, as shown in FIG. 16, the cradle 55 is constituted by a microcomputer, an exclusive printed circuit board, such as an FPGA (Field Programmable Gate Array), etc., etc., other than the connecting connector 55a to be coupled to the connector 39 of the radiographic image capturing apparatus 1, which is currently inserted into the insertion opening as aforementioned, and is provided with a calculating section 55b having a storage section (not shown in the drawings). Further, the calculating section 55b is coupled to the connecting connector 55a.

Further, according to the "PATTERN 1", on an occasion that the radiographic image capturing apparatus 1a, serving as the original apparatus, is brought back to the factory or the like due to its repairing work or the like, or another occasion more previous than the above, the radiographic image capturing apparatus 1a, serving as the original apparatus, is inserted into the cradle 55 so as to make the storage section store the information of the first correction data sets "α" and the second correction data sets "α*" in regard to the radiographic image capturing apparatus 1a concerned, in advance.

In this connection, although an embodiment of the "PATTERN 1" is so constituted that the storage section of the calculating section 55b of the cradle 55 is made to store only the information of the first correction data sets "α" and the second correction data sets "α*" in regard to the radiographic image capturing apparatus 1a, serving as the original apparatus, therein, for instance, it is also applicable that the system is so constituted that the storage section of the cradle 55 is made to store information including a plurality of groups of the first correction data sets "α" and a plurality of groups of the second correction data sets "α*" in regard to all of the radiographic image capturing apparatuses 1, which have been introduced (which have been registered through the cradle 55 concerned) into the image capturing room Ra1 in which the cradle 55 concerned is installed.

In the configuration of the "PATTERN 1", when the second correction data sets "α*", such as the gain correction values G, etc., are updated at the time of the maintenance operation of each of the radiographic image capturing apparatuses 1, the updated second correction data sets "α*", etc. are stored into the storage section of the calculating section 55b of the cradle 55 in the overwrite saving mode in which the updated second correction data sets "α*", etc., are overwritten over the original second correction data sets "α*" in regard to the radiographic image capturing apparatus 1 concerned. In this connection, in such the case that the management apparatus S manages the information of the first correction data sets "α" and the second correction data sets "α*" in regard to each of the radiographic image capturing apparatuses 1 as in the present embodiment, the updated second correction data sets "α*" are also transmitted to the management apparatus S, so as to store them therein according to the overwrite saving mode.

Further, as shown in FIG. 16, the cradle 55 is provided with an inputting device 55c, such as a keyboard, etc., which is coupled to the calculating section 55b. Still further, the cradle 55 is so constituted that it is possible for the operator to input the cassette ID, serving as the identification information of the original radiographic image capturing apparatus 1a, into the calculating section 55b through the inputting device 55c.

Still further, when the radiographic image capturing apparatus 1b is introduced as the replacement use apparatus for the radiographic image capturing apparatus 1a, serving as the original apparatus, the following processing are conducted in the cradle 55.

Concretely speaking, when the radiographic image capturing apparatus 1b for replacement use is inserted into insertion opening of the cradle 55, as shown in FIG. 16, the connector 39 of the radiographic image capturing apparatus 1b for replacement use is coupled to the connecting connector 55a of the cradle 55. Then, in the abovementioned state, the image capturing operator, such as a radiologist, etc., input the cassette ID, serving as the identification information of the original radiographic image capturing apparatus 1a, which has been replaced by the radiographic image capturing apparatus 1b for replacement use (in other words, the radiographic image capturing apparatus 1a, which has been carried out for the purpose of its repairing work or the like).

Successively, based on the cassette ID inputted in the above, the calculating section 55b of the cradle 55 reads out the first correction data sets "α" respectively corresponding to the radiation detecting elements 7 in regard to the radiographic image capturing apparatus 1a, serving as the original apparatus, (in other words, the first correction data sets of the radiographic image capturing apparatus 1a, which has been established at the time of the factory default setting operation) and the second correction data sets "α*" (in other words, the second correction data sets established at the time when introducing the radiographic image capturing apparatus 1a, serving as the original apparatus, or the second correction data sets updated at the time when implementing the maintenance operation thereof), from the storage section.

Still successively, the calculating section 55b reads out the first correction data sets "β", respectively corresponding to the radiation detecting elements 7 in regard to the radiographic image capturing apparatus 1b concerned for replacement use, from the radiographic image capturing apparatus 1b for replacement use, which has been inserted into the cradle 55 through the connecting connector 55a and the connector 39.

As aforementioned, based on the image data sets D (and the offset data sets O) that have been acquired at the time of the factory default setting operation by uniformly irradiating the predetermined amount of radiation, serving as parallel light, onto the radiation incident surface R (refer to the schematic diagram shown in FIG. 1) of the radiographic image capturing apparatus, each of the first correction data sets "α" or each of the first correction data sets "β" is established in regard to each of the radiation detecting elements 7, so that the values of the final image data D* calculated according to the Equation (1) are made to be the same as each other allover the radiation detecting elements 7.

Further, according to the radiation characteristics of the radiation source 52 currently installed into the image capturing room Ra, the second correction data sets "α*" are established by correcting each of the first correction data sets "α" for every one of the radiation detecting elements 7, so that the values of the final image data D* based on the image data sets D (and the offset data sets O), read in the above, are made to be the same as each other allover the radiation detecting elements 7.

Based on the abovementioned, it would be possible to calculate the second correction data sets "β*" in regard to the radiographic image capturing apparatus 1b for replacement use, by changing the values of the first correction data sets "β" at the same rate as that to be employed for changing the first correction data sets "α" to the second correction data sets "α*" in regard to the radiographic image capturing apparatus 1a, serving as the original apparatus.

In other words, for instance, in the case that the second correction data sets "β*" are such the multiplying-type correction data sets that are to be applied by employing the multiplying operation or the dividing operation for the image data sets D, as the gain correction value G in the Equation (1) aforementioned, the ratio of the first correction data sets "β" and the second correction data sets "β*", in regard to the radiographic image capturing apparatus 1b for replacement use, should be equal to the ratio of the first correction data sets "α" and the second correction data sets "α*", in regard to the radiographic image capturing apparatus 1a serving as the original apparatus, as expressed by the following Equation (2).

$$\beta : \beta^* = \alpha : \alpha^* \tag{2}$$

Accordingly, when the second correction data sets "β*" are the multiplying-type correction data sets, based on the first correction data sets "β", read from the radiographic image capturing apparatus 1b for replacement use, and the first correction data sets "α" and second correction data sets "α*", read from the storage section of the radiographic image capturing apparatus 1a serving as the original apparatus, it becomes possible to calculate the second correction data sets "β*" respectively corresponding to the radiation detecting elements 7 provided in the radiographic image capturing apparatus 1b for replacement use, through an arithmetic calculation process, by conducting the calculation according to Equation (3), indicated as follow, for every one of the radiation detecting elements 7.

$$\beta^* = \beta \times \alpha^* / \alpha \tag{3}$$

Further, for instance, when the arithmetic calculations according to the aforementioned Equation (1), etc., are conducted, sometimes, the arithmetic calculation process may be so constituted that, based on not only the offset data sets O, but also the radiation characteristics of the radiation source 52 that has actually irradiated the radiation onto the radiographic image capturing apparatus 1, predetermined offset data sets O* are added to or subtracted from the values of image data sets D or the other values of (D−O), which are derived by subtracting the offset data sets O from the image data sets D, so as to conduct the arithmetic calculations according to the aforementioned Equation (1), etc.

In the above case, the offset data sets O* can be regarded as a kind of the second correction data sets "β*". Further, the offset data sets O* are defined as the adding-type correction data sets that are applied by employing the adding operation or the subtracting operation for the image data sets D. As described in the above, the second correction data sets "β*" include not only the multiplying-type correction data sets, such as the gain correction values G aforementioned, etc., but also the adding-type correction data sets, such as the offset data sets O* abovementioned.

Further, as expressed by Equation (4) indicated in the following, it should be established that the differences between the first correction data sets "β" and the second correction data sets "β*", in regard to the radiographic image capturing apparatus 1b for replacement use, are equal to the other differences between the first correction data sets "α" and the second correction data sets "α*" in regard to the radiographic image capturing apparatus 1a, serving as the original apparatus.

$$\beta^* - \beta = \alpha^* - \alpha \tag{4}$$

Accordingly, when the second correction data sets "β*" are the adding-type correction data sets, based on the first correction data sets "β", read from the radiographic image capturing apparatus 1b for replacement use, and the first correction data sets "α" and second correction data sets "α*", read from the storage section of the radiographic image capturing apparatus 1a serving as the original apparatus, it becomes possible to calculate the second correction data sets "β*" respectively corresponding to the radiation detecting elements 7 provided in the radiographic image capturing apparatus 1b for replacement use, through an arithmetic calculation process, by conducting the calculation according to Equation (5), indicated as follow, for every one of the radiation detecting elements 7.

$$\beta^* = \beta(\alpha^* - \alpha) \tag{5}$$

In this connection, with respect to each of the second correction data sets "β*", it is necessary to determine in advance whether the second correction data sets "β*", to be calculated in regard to the radiographic image capturing apparatus 1b for replacement use, are the multiplying-type correction data or the adding-type correction data, Trough the abovementioned process, based on the first correction data sets "β", read from the radiographic image capturing apparatus 1b for replacement use, and the first correction data sets "α" and the second correction data sets "α*" read from the storage section of the radiographic image capturing apparatus 1a, serving as the original apparatus, the calculating section 55b of the cradle 55 implements the arithmetic calculating operations according to the Equation (3) or the Equation (5), so as to calculate the second correction data sets "β*" respectively corresponding to the radiation detecting elements 7 provided in the radiographic image capturing apparatus 1b for replacement use.

Successively, the calculating section 55b of the cradle 55 establishes the second correction data sets "β*", calculated in the above, in regard to the radiographic image capturing apparatus 1b for replacement use.

According to the radiographic image capturing system 50 configured as abovementioned, since the cradle 55 conducts the processing for calculating and setting the second correction data sets "β*" in regard to the radiographic image capturing apparatus 1b for replacement use, it becomes unnecessary for the console C to conduct the abovementioned processing for calculating and setting the second correction data sets "β*".

Accordingly, for instance, when the processing for calculating and setting the second correction data sets "β*", in regard to the radiographic image capturing apparatus 1b for replacement use, are to be implemented in the image capturing room Ra2 currently designated by the console C1, even if the console C1 is busy for conducting the image capturing operation in the image capturing room Ra1, the processing for calculating and setting the second correction data sets "β*" can be implemented in the cradle 55. Therefore, it becomes possible to eliminate such the problem that it is impossible to actually implement the abovementioned processing until the console C1 is released from the image capturing operation in the image capturing room Ra1.

Further, it is possible for the radiologist or the like to calculate and establish the second correction data sets "β*" in regard to the radiographic image capturing apparatus 1b for replacement use, only by inserting the radiographic image capturing apparatus 1b for replacement use into the cradle 55 and inputting the cassette ID of the radiographic image capturing apparatus 1a, serving as the original apparatus, without conducting such the operations for making the radiation source 52, currently installed in the image capturing room Ra2, irradiate the radiation onto the radiographic image capturing apparatus 1b for replacement use so as to read out the image data sets D, etc.

Accordingly, it becomes possible for the radiologist or the like to conduct the operations for calculating and setting the second correction data sets "β*" in regard to the radiographic image capturing apparatus 1b for replacement use in very easy way, and therefore, the radiographic image capturing system 50, embodied in the present invention, becomes very convenient and user-friendly for the radiologist or the like.

In this connection, as aforementioned, a plurality of cradles 55 is installed into a plurality of image capturing rooms Ra, respectively. Accordingly, as well as in "PATTERN 2" or "PATTERN 3" detailed later, it is possible to configure the system in such a manner that the cradle 55 installed in a certain image capturing room Ra can calculate and establish the second correction data sets "β*" only corresponding to the radiation source 52 currently installed into the image capturing room Ra concerned (in case that a plurality of radiation sources 52 is installed into the image capturing room Ra, all of the radiation source 52 residing in the image capturing room Ra concerned).

When the system is configured as abovementioned, only by bringing the concerned radiographic image capturing apparatus 1b for replacement use into each of the image capturing rooms Ra and inserting it into the cradle 55 in each of the image capturing rooms Ra, it is possible for the radiologist or the like to conduct the operation for setting the second correction data sets "β" corresponding to each of the radiation sources 52 in regard to the radiographic image capturing apparatus 1b for replacement use.

Further, it is also possible to configure the system in such a manner that each of the cradles 55 installed in each of the image capturing rooms Ra stores in advance the first correction data sets "α" and plural groups of second correction data sets "β*" respectively corresponding to all of the radiation sources 52 residing within the system (in the case of the schematic diagram shown in FIG. 7, all of the radiation sources 52 respectively installed in the image capturing rooms Ra1 through Ra3), in regard to each of the radiographic image capturing apparatuses 1.

According to the system configured as abovementioned, only by inserting the radiographic image capturing apparatus 1b for replacement use into, for instance, the cradle 55 of the image capturing room Ra2 and inputting the cassette ID of the radiographic image capturing apparatus 1a, serving as the original apparatus, it becomes possible for the radiologist or the like to establish the second correction data sets "β*" corresponding to each of all of the radiation sources 52 respectively installed in the image capturing rooms Ra1 through Ra3 at a time, instead of only the radiation source 52 installed in the image capturing room Ra2.

Accordingly, it becomes possible for the radiologist or the like to conduct the operations for calculating and setting the second correction data sets "β*" in regard to the radiographic image capturing apparatus 1b for replacement use in very easy way, and therefore, the radiographic image capturing system 50, embodied in the present invention, becomes very convenient and user-friendly for the radiologist or the like.

In this connection, in the abovementioned case, it is also possible that the system is so constituted that, instead of all of the image capturing rooms Ra1 through Ra3, a range of the image capturing rooms Ra in which the concerned radiographic image capturing apparatus 1b for replacement use is to be employed (for instance, only the image capturing room Ra1 and Ra2) is established in advance, so that only the second correction data sets "β*" corresponding to each of the radiation sources 52 respectively installed in the image capturing rooms Ra, established in advance, is to be established in the cradle 55 installed in one of the image capturing rooms Ra.

Further, when the system is so constituted that the management apparatus S manages (controls) the first correction data sets "α" and the second correction data sets "α*" in regard to each of the radiographic image capturing apparatuses 1, as in the present embodiment, the calculating section 55b of the cradle 55 is so constituted that the calculating section 55b transmits the first correction data sets "β", read from the radiographic image capturing apparatus 1b for replacement use, and the second correction data sets "β*" calculated therein, in addition to the cassette ID of the radiographic image capturing apparatus 1b for replacement use, to the management apparatus S, so as to make the management apparatus S manage the first correction data sets "β" and the second correction data sets "β*", as well.

<Pattern 2>

In the abovementioned embodiment of "PATTERN 1", such the case that all of the processing for calculating and setting the second correction data sets "β*" in regard to the radiographic image capturing apparatus 1b for replacement use are conducted by the cradle 55, have been detailed in the foregoing. However, when the management apparatus S manages the first correction data sets "α" and the second correction data sets "α*" in regard to each of the radiographic image capturing apparatuses 1, as in the present embodiment, it is unnecessary for the cradle 55 to store and manage those information. Instead, the system can be so constituted that the necessary information can be acquired from the management apparatus S.

Accordingly, in this "PATTERN 2", on an occasion that the radiographic image capturing apparatus 1b for replacement use is introduced as the replacement use apparatus for the radiographic image capturing apparatus 1a, serving as the original apparatus, when the radiographic image capturing apparatus 1b for replacement use is inserted into the cradle 55 and the cassette ID of the radiographic image capturing apparatus 1a, serving as the original apparatus, is inputted, the calculating section 55b of the cradle 55 transmits the cassette ID of the radiographic image capturing apparatus 1a, serving as the original apparatus, to the management apparatus S, and then, the cradle 55 acquires the first correction data sets "α" and the second correction data sets "α*" in regard to the radiographic image capturing apparatus 1a, serving as the original apparatus.

Successively, the calculating section 55b of the cradle 55 reads out the first correction data sets "β" from the radiographic image capturing apparatus 1b for replacement use, and then, substitutes the first correction data sets "β" in regard to the radiographic image capturing apparatus 1b for replacement use, and the first correction data sets "α" and the second correction data sets "α*" in regard to the radiographic image capturing apparatus 1a, serving as the original apparatus, into the aforementioned Equation (3) and Equation (5), so as to calculate the second correction data sets "β*" respectively corresponding to the radiation detecting elements 7 provided in the radiographic image capturing apparatus 1b for replacement use. Still successively, the calculating section 55b of the cradle 55 establishes the second correction data sets "β*", calculated in the above, in regard to the concerned radiographic image capturing apparatus 1b for replacement use.

According to the system configured as abovementioned, since the processing for calculating and setting the second correction data sets "β*" in regard to the radiographic image capturing apparatus 1b for replacement use can be implemented in the cradle 55, it becomes unnecessary for the radiologist or the like to conduct the abovementioned calculating and setting processing from the console C, and it becomes possible to eliminate such the problem that it is impossible to actually implement the abovementioned processing until the console C1 is released from the currently conducting operations.

Further, since the second correction data sets "β*" in regard to the radiographic image capturing apparatus 1b for replacement use can be calculated and established, only by inserting the radiographic image capturing apparatus 1b for replacement use into the cradle 55 and inputting the cassette ID of the radiographic image capturing apparatus I a, serving as the original apparatus, it becomes possible for the radiologist or the like to conduct the operations for calculating and setting the second correction data sets "β*" in regard to the radiographic image capturing apparatus 1b for replacement use in very easy way, and therefore, the radiographic image capturing system 50, embodied in the present invention, becomes very convenient and user-friendly for the radiologist or the like.

Further, it becomes unnecessary for the cradle 55 to store and manage the first correction data sets "α" and the second correction data sets "α*" in regard to the radiographic image capturing apparatus 1a, serving as the original apparatus, and the system can be so constituted that the management apparatus S totally manages (controls) them.

Accordingly, the embodiment of "PATTERN 2" yields such a advantageous effect that it also becomes unnecessary for the radiologist or the like to conduct such the operations for inserting the radiographic image capturing apparatus 1a, serving as the original apparatus, into the cradle 55 so as to make the storage section store the information of the first correction data sets "α" and the second correction data sets "α*" in regard to the radiographic image capturing apparatus 1a concerned, before the radiographic image capturing apparatus 1 a, serving as the original apparatus, is brought back to the factory or the like due to its repairing work or the like, though it is necessary to conduct the abovementioned operations in the previous embodiment of "PATTERN 1".

<Pattern 3>

In abovementioned "PATTERN 1" and "PATTERN 2", such the case that the cradle 55 conducts the operation for calculating the second correction data sets "β*" in regard to the radiographic image capturing apparatus 1b for replacement use has been described. However, it is also possible that the system is so constituted that the management apparatus S conducts the calculating processing abovementioned.

Accordingly, in this case, when accepting the radiographic image capturing apparatus 1b for replacement use, serving as the replacement apparatus of the original radiographic image capturing apparatus 1a and inserted therein, the cradle 55 reads out the first correction data sets "β" from the radiographic image capturing apparatus 1b for replacement use, and then, transmits the first correction data sets "β" above-read, and the cassette ID serving as the identification information of the original radiographic image capturing apparatus 1a and inputted through the inputting device, to the management apparatus S.

Receiving the first correction data sets "β" and the cassette ID sent from the cradle 55, the management apparatus S reads out the first correction data sets "α" and the second correction data sets "α*", in regard to the original radiographic image capturing apparatus 1a represented by the identification information of the cassette ID received, from the storage section, and conducts the arithmetic calculating operations employing the Equation (3) and the Equation (5) aforementioned, based on the first correction data sets "α" and the second correction data sets "α*", both above-read, and the first correction data sets "β" in regard to the radiographic image capturing apparatus 1b for replacement use, so as to calculate the second correction data sets "β*" in regard to the radiographic image capturing apparatus 1b for replacement use.

Successively, the management apparatus S transmits the second correction data sets "β*" calculated in the above in regard to the radiographic image capturing apparatus 1b for replacement use, to the image capturing room Ra (for instance, image capturing room Ra2), into which the cradle 55 concerned is currently installed, so as to establish the second correction data sets "β*" for the radiographic image capturing apparatus 1b currently inserted into the cradle 55, through the cradle 55 concerned.

According to the system configured as abovementioned, since the processing for calculating and setting the second correction data sets "β*" in regard to the radiographic image capturing apparatus 1b for replacement use can be implemented by the management apparatus S in such a state that the radiographic image capturing apparatus 1b for replacement use is inserted into the cradle 55, it becomes unnecessary for the radiologist or the like to conduct the abovementioned calculating and setting processing from the console C, and it becomes possible to eliminate such the problem that it is impossible to actually implement the abovementioned processing until the console C1 is released from the currently conducting operations.

Further, since the second correction data sets "β*" in regard to the radiographic image capturing apparatus 1b for replacement use can be calculated and established, only by inserting the radiographic image capturing apparatus 1b for replacement use into the cradle 55 and inputting the cassette ID of the radiographic image capturing apparatus 1a, serving as the original apparatus, it becomes possible for the radiologist or the like to conduct the operations for calculating and setting the second correction data sets "β*" in regard to the radiographic image capturing apparatus 1b for replacement use in very easy way, and therefore, the radiographic image capturing system 50, embodied in the present invention, becomes very convenient and user-friendly for the radiologist or the like.

Further, it becomes unnecessary for the cradle 55 to store and manage the first correction data sets "α" and the second correction data sets "α*" in regard to the radiographic image capturing apparatus 1a, serving as the original apparatus, and the system can be so constituted that the management apparatus S totally manages (controls) them, and in addition, management apparatus S also conducts the processing for calculating the second correction data sets "β*".

Therefore, according to "PATTERN 3", since it becomes unnecessary for the cradle 55 to conduct the processing for calculating the second correction data sets "β*" in regard to the radiographic image capturing apparatus 1b for replacement use as conducted in "PATTERN 1" and "PATTERN 2", it becomes possible to considerably alleviate the processing burden to be loaded onto the calculating section 55b provided in the cradle 55. Further, it may be possible to omit the calculating section 55b from the cradle 55.

Further, since it becomes unnecessary for the cradle 55 to store and maintain the information of first correction data sets "β" of the radiographic image capturing apparatus 1b for replacement use, the first correction data sets "α" and the second correction data sets "α*" of the radiographic image capturing apparatus 1a, serving as the original apparatus, the embodiment of "PATTERN 3" yields such a advantageous effect that it becomes unnecessary to provide the cradle 55 with the storage section.

As described in the foregoing, the radiographic image capturing system 50, embodied in the present invention, is so constituted that, based on the first correction data sets "β" in regard to the radiographic image capturing apparatus 1b for the replacement use, and the first correction data sets "α" and the second correction data sets "α*" in regard to the radiographic image capturing apparatus 1a, serving as the original apparatus, either the management apparatus S, or the cradle 55 installed into the image capturing room Ra, calculates and establishes the second correction data sets "β*" in regard to the radiographic image capturing apparatus 1b for replacement use, corresponding to the radiation source 52 residing in the image capturing room Ra in which the cradle 55 is installed.

Accordingly, it becomes unnecessary for the radiologist or the like to purposely irradiate the radiation emitted from the radiation source 52, currently residing in the image capturing room Ra, onto the radiographic image capturing apparatus 1b of the replacement use, which is to be temporarily employed as the replacement for the radiographic image capturing apparatus 1a serving as the original apparatus, so as to established the second correction data sets "β*" in regard to the radiographic image capturing apparatus 1b of the replacement use. Further, only by inserting the radiographic image capturing apparatus 1b into the cradle 55 and inputting the cassette ID, serving as the identification information of the radiographic image capturing apparatus 1a, serving as the original apparatus, it becomes possible for the radiologist or the like to established the second correction data sets "β*" concerned.

Further, since either the cradle 55 or the management apparatus S applies the relationship between the first correction data sets "α" and the second correction data sets "α*", in regard to the radiographic image capturing apparatus 1a serving as the original apparatus, to the relationship between the first correction data sets "β" and the second correction data sets "β*", in regard to the radiographic image capturing apparatus 1b for replacement use, so as to calculate and establish the second correction data sets "β*", it becomes possible for the radiologist or the like to conduct the operations for calculating and setting the second correction data sets "β*" in regard to the radiographic image capturing apparatus 1b for replacement use in very easy way, and therefore, the radiographic image capturing system 50, embodied in the present invention, becomes very convenient and user-friendly for the radiologist or the like.

Still further, according to the radiographic image capturing system 50, embodied in the present invention, since either the cradle 55 or the management apparatus S, instead of the console C, establishes the second correction data sets "β*" in regard to the radiographic image capturing apparatus 1b for replacement use, for instance, even in such the case that a certain radiologist or the like operates the console C1 to designate the image capturing rooms Ra1 and Ra2, and the console C1 is correlated with the image capturing rooms Ra1 and Ra2, for instance, it becomes possible for another radiologist to insert the radiographic image capturing apparatus 1b for replacement use into the cradle 55 currently residing in the image capturing room Ra2, so as to establish the second correction data sets "β*" in regard to the radiographic image capturing apparatus 1b for replacement use.

As described in the foregoing, according to the radiographic image capturing system 50, embodied in the present invention, even if the console C is busy for conducting the image capturing operation, it becomes possible for the radiologist or the like to conduct the operations for setting the second correction data sets "β*" in regard to the radiographic image capturing apparatus 1b for replacement use, and therefore, the radiographic image capturing system 50, embodied in the present invention, becomes very convenient and user-friendly for the radiologist or the like.

In this connection, it is needless to say that the scope of the present invention is not limited to the embodiments described in the foregoing. Modifications and additions made by a skilled person without departing from the spirit and scope of the invention shall be included in the scope of the present invention.

According to the radiographic image capturing system embodied in the present invention, the following advantageous effects can be attained.

(1) It becomes possible to constitute the radiographic image capturing system, in such a manner that, based on the first β-correction data in regard to the radiographic image capturing apparatus for the replacement use, and the first α-correction data and the second α*-correction data in regard to the radiographic image capturing apparatus serving as the original apparatus, either the management apparatus, or the cradle installed into the image capturing room, calculates and establishes the second β*-correction data in regard to the radiographic image capturing apparatus for replacement use, corresponding to the radiation source residing in the image capturing room in which the cradle is installed.

(2) Thanks to the abovementioned novel configuration, it becomes unnecessary for the radiologist or the like to purposely irradiate the radiation emitted from the radiation source, currently residing in the image capturing room, onto the radiographic image capturing apparatus of the replacement use, which is to be temporarily employed as the replacement use apparatus for the radiographic image capturing apparatus serving as the original apparatus, so as to established the second β*-correction data in regard to the radiographic image capturing apparatus for replacement use. Instead, only by inserting the radiographic image capturing apparatus into the cradle and inputting the identification information of the radiographic image capturing apparatus serving as the original apparatus, it becomes possible for the radiologist or the like to established the second β*-correction data concerned.

(3) In addition to the above, since either the cradle or the management apparatus applies the relationship between the first α-correction data and the second α*-correction data, in regard to the radiographic image capturing apparatus serving as the original apparatus, to the relationship between the first β-correction data and the second β*-correction data, in regard to the radiographic image capturing apparatus for replacement use, so as to calculate and establish the second β*-correction data, it becomes possible for the radiologist or the like to conduct the operations for calculating and setting the second β*-correction data in regard to the radiographic image capturing apparatus for replacement use in very easy way, and therefore, the radiographic image capturing system, embodied in the present invention, becomes very convenient and user-friendly for the radiologist or the like, concerned. (4) Since either the cradle or the management apparatus, instead of the console, establishes the second β*-correction data in regard to the radiographic image capturing apparatus for replacement use, for instance, even in such the case that a certain radiologist or the like operates a console to designate a certain image capturing room, and the designated console is correlated with image capturing mom concerned, for instance, it becomes possible for another radiologist to insert the radiographic image capturing apparatus for replacement use into another cradle currently residing in another image capturing room, so as to establish the second β*-correction data in regard to the radiographic image capturing apparatus for replacement use.

(5) As a result of the abovementioned feature of the present invention, even if the console is busy for conducting the image capturing operation, it becomes possible for the radiologist or the like to conduct the operations for establishing the second β*-correction data in regard to the radiographic image capturing apparatus for replacement use, and therefore, the radiographic image capturing system, embodied in the present invention, becomes very convenient and user-friendly for the radiologist or the like.

Incidentally, the aforementioned method for simplifying the process of introducing the FPD cassette for replacement use, by using the first α-correction data and the second α*-correction data of the FPD cassette originally residing in the image capturing room, is also available for such a case that a new FPD cassette is introduced into the image capturing room concerned, in addition to the FPD cassette introduced in advance into the image capturing room currently existing.

While the preferred embodiments of the present invention have been described using specific term, such description is for illustrative purpose only, and it is to be understood that changes and variations may be made without departing from the spirit and scope of the appended claims.

What is claimed is:

1. A radiographic image capturing system, comprising:
a radiographic image capturing apparatus that is provided with a plurality of radiation detecting elements arranged in a two dimensional pattern, so as to reads out each of electric signals, generated in each of the radiation detecting elements by irradiating radiation thereon, as image data;

a radiation source to emit the radiation to be irradiated onto the radiographic image capturing apparatus;

a cradle that is provided in an image capturing room or a front room; and a console to create a radiographic image based on the image data transmitted from the radiographic image capturing apparatus;

wherein the cradle reads out first α-correction data, established at a time of factory default setting operation, and second α*-correction data, established corresponding to the radiation source currently residing in the image capturing mom, from the radiographic image capturing apparatus, which is currently inserted into the cradle, so as to store the first α-correction data and the second α*-correction data therein; and wherein, when a radiographic image capturing apparatus for replacement use, serving as a replacement use apparatus for the radiographic image capturing apparatus, is inserted into the cradle, the cradle reads out first β-correction data, established at a time of factory default setting operation, from the radiographic image capturing apparatus for replacement use, and then, based on the first β-correction data read from the radiographic image capturing apparatus for replacement use, and the first α-correction data and second β*-correction data, both read from the radiographic image capturing apparatus, serving as an original apparatus, the cradle calculates second β*-correction data corresponding to the radiation source currently residing in the image capturing room, so as to establish the second β*-correction data above-calculated in regard to the radiographic image capturing apparatus for replacement use.

2. The radiographic image capturing system of claim 1, wherein, when reading out the first α-correction data and the second α*-correction data from the radiographic image capturing apparatus currently inserted, the cradle also reads out identification information for identifying the radiographic image capturing apparatus serving as the original apparatus, so as to store the identification information, the first α-correction data and the second α*-correction data, therein, while correlating the identification information with the first α-correction data and the second α*-correction data; and wherein, when the radiographic image capturing apparatus for replacement use, serving as the replacement use apparatus for the radiographic image capturing apparatus serving as the original apparatus, is inserted into the cradle, and the identification information for identifying the radiographic image capturing apparatus serving as the original apparatus is inputted through a inputting device, the cradle calculates the second β*-correction data corresponding to the radiation source currently residing in the image capturing room, based on the first β-correction data in regard to the radiographic image capturing apparatus for replacement use, and the first α-correction data and the second α*-correction data read out from the radiographic image capturing apparatus serving as the original apparatus and designated by the identification information, so as to establish the second β*-correction data in regard to the radiographic image capturing apparatus for replacement use.

3. The radiographic image capturing system of claim 1, further comprising:

a management apparatus that manages the first α-correction data and the second α*-correction data in regard to the radiographic image capturing apparatus serving as the original apparatus;

wherein, when the radiographic image capturing apparatus for replacement use, serving as the replacement use apparatus for the radiographic image capturing apparatus serving as the original apparatus, is inserted into the cradle, instead of storing the first α-correction data and the second α*-correction data, in regard to the radiographic image capturing apparatus serving as the original apparatus, in its own, the cradle acquires the first α-correction data and the second α*-correction data from the management apparatus, and then, calculates the second β*-correction data so as to establish the second β*-correction data in regard to the radiographic image capturing apparatus for replacement use.

4. The radiographic image capturing system of claim 3, wherein, when reading out the first α-correction data and the second α*-correction data from the radiographic image capturing apparatus currently inserted, the cradle also reads out identification information for identifying the radiographic image capturing apparatus serving as the original apparatus, so as to transmit the identification information, the first α-correction data and the second α*-correction data, to the management apparatus, while correlating the identification information with the first α-correction data and the second α*-correction data; and wherein, when the radiographic image capturing apparatus for replacement use, serving as the replacement use apparatus for the radiographic image capturing apparatus serving as the original apparatus, is inserted into the cradle, and the identification information for identifying the radiographic image capturing apparatus serving as the original apparatus is inputted through a inputting device, the cradle transmits the identification information to the management apparatus so as to acquire the first a-correction data and the second α*-correction data in regard to the radiographic image capturing apparatus serving as the original apparatus, and then, calculates the second β*-correction data in regard to the radiographic image capturing apparatus for replacement use, so as to establish the second β*-correction data for the radiographic image capturing apparatus for replacement use.

5. The radiographic image capturing system of claim 1, further comprising:

a management apparatus that manages the first α-correction data and the second α*-correction data in regard to the radiographic image capturing apparatus serving as the original apparatus;

wherein, when completing operations for calculating the second β*-correction data in regard to the radiographic image capturing apparatus for replacement use, the cradle transmits the first β-correction data, read from the radiographic image capturing apparatus for replacement use, and the second β*-correction data, in addition to identification information for identifying the radiographic image capturing apparatus for replacement use, to the management apparatus so as to make the management apparatus manage the first β-correction data and the second β*-correction data in regard to the radiographic image capturing apparatus for replacement use.

6. The radiographic image capturing system of claim 2, further comprising:

a management apparatus that manages the first α-correction data and the second α*-correction data in regard to the radiographic image capturing apparatus serving as the original apparatus;

wherein, when the radiographic image capturing apparatus for replacement use, serving as the replacement use apparatus for the radiographic image capturing apparatus serving as the original apparatus, is inserted into the cradle, the cradle reads out the first β-correction data from the radiographic image capturing apparatus for replacement use, and then, transmits the first β-correction data to the management apparatus, instead of calculating the second β*-correction data in regard to the radiographic image capturing apparatus for replacement use within the cradle; and wherein the management apparatus calculates the second β*-correction data in regard to the radiographic image capturing apparatus for replacement use, based on the first β-correction data transmitted from the cradle in regard to the radiographic image capturing apparatus for replacement use, and the first α-correction data and the second α*-correction data in regard to the radiographic image capturing apparatus serving as the original apparatus, so as to establish the second β*-correction data above-calculated in regard to the radiographic image capturing apparatus for replacement use, through the cradle.

7. The radiographic image capturing system of claim 6, wherein, when the radiographic image capturing apparatus for replacement use, serving as the replacement use apparatus for the radiographic image capturing apparatus serving as the original apparatus, is inserted into the cradle, and the identification information for identifying the radiographic image capturing apparatus serving as the original apparatus is inputted through a inputting device, the cradle transmits the first β-correction data, read from the management apparatus in regard to the radiographic image capturing apparatus for replacement use, and the identification information of the radiographic image capturing apparatus serving as the original apparatus; and wherein the management apparatus calculates the second β*-correction data in regard to the radiographic image capturing apparatus for replacement use, based on the first β-correction data transmitted from the cradle in regard to the radiographic image capturing apparatus for replacement use, and the first α-correction data and the second α*-correction data transmitted from the cradle in regard to the radiographic image capturing apparatus serving as the original apparatus, which corresponds to the identification information, so as to establish the second β*-correction data above-calculated in regard to the radiographic image capturing apparatus for replacement use, through the cradle.

8. The radiographic image capturing system of claim 1, further comprising:

a management apparatus that manages the first α-correction data and the second α*-correction data in regard to the radiographic image capturing apparatus serving as the original apparatus; and a plurality of the radiation sources;

wherein either the cradle or the management apparatus stores plural groups of the second α*-correction data, which respectively correspond to the radiation sources, in addition to the first α-correction data in regard to the radiographic image capturing apparatus serving as the original apparatus, therein.

* * * * *